(12) United States Patent
Marti et al.

(10) Patent No.: US 6,220,099 B1
(45) Date of Patent: Apr. 24, 2001

(54) APPARATUS AND METHOD FOR PERFORMING NON-DESTRUCTIVE INSPECTIONS OF LARGE AREA AIRCRAFT STRUCTURES

(75) Inventors: David Kenneth Marti, Suffield, CT (US); Gene Joseph Descant, Feeding Hills, MA (US); Steven M. Craig, Terryville, CT (US)

(73) Assignee: CE Nuclear Power LLC, Windsor, CT (US)

( * ) Notice: Subject to any disclaimer, the term of this patent is extended or adjusted under 35 U.S.C. 154(b) by 0 days.

(21) Appl. No.: 09/231,668

(22) Filed: Jan. 15, 1999

Related U.S. Application Data
(60) Provisional application No. 60/074,876, filed on Feb. 17, 1998.

(51) Int. Cl.[7] .................................................. G01N 29/04
(52) U.S. Cl. .............................................................. 73/633
(58) Field of Search .............................. 73/618, 619, 620, 73/621, 622, 627, 629, 633, 634

(56) References Cited

U.S. PATENT DOCUMENTS

| | | | |
|---|---|---|---|
| 4,170,145 | * 10/1979 | Kennedy et al. | 73/618 |
| 4,304,133 | 12/1981 | Feamster, III | 73/633 |
| 4,434,659 | * 3/1984 | Kurtz et al. | 73/620 |
| 4,677,916 | 7/1987 | Dodd | 104/118 |
| 4,891,986 | * 1/1990 | Teagle | 73/634 |
| 5,029,476 | * 7/1991 | Metala et al. | 73/620 |
| 5,576,492 | * 11/1996 | Phalin | 73/618 |

FOREIGN PATENT DOCUMENTS
2 263 777    8/1993   (GB) .

OTHER PUBLICATIONS
"Appendix A—Equipment Specification for an Automated Large Area Aircraft Inspection System", Dec. 1995.*

"Part II—Large Area Aircraft Inspection System Technical Description" (ABB AMDATA Proposal 96–609).*

"Addendum to Technical Proposal for an Automated Large Area Aircraft Inspection System" (Abb AMDATA Proposal 96–609).*

"Part III—Response to the Purchase Specification" (ABB AMDATA Proposal 96–609).*

* cited by examiner

Primary Examiner—Helen Kwok
(74) Attorney, Agent, or Firm—Rader, Fishman & Grauer

(57) ABSTRACT

A surface scanner for conducting non-destructive inspection of complex surface structures and configurations. The scanner includes two flexible tracks, each fitted with a motor driven tractor assembly. A rigid beam track spans the two flexible tracks. The rigid beam track is coupled to each flexible track tractor assembly by articulating joints that permit movement at the joints along at least three independent axes. The rigid beam supports a third motorized tractor. This third tractor supports a compliant thruster assembly that deploys gimbaled mechanical impedance, ultrasonic and eddy current inspection probes. The movement of the scanner is controlled by a scan control system that includes both hardware and software for controlling the movement of the scanner over the surface to be inspected. The software also includes a teach mode that permits an operator to preprogram the scan pattern for the surface to be inspected using a global coordinate system, referencing points on the surface and the data display using an identical coordinate system. The scanner also includes a data acquisition and analysis system that control scanner functions and operations.

98 Claims, 10 Drawing Sheets

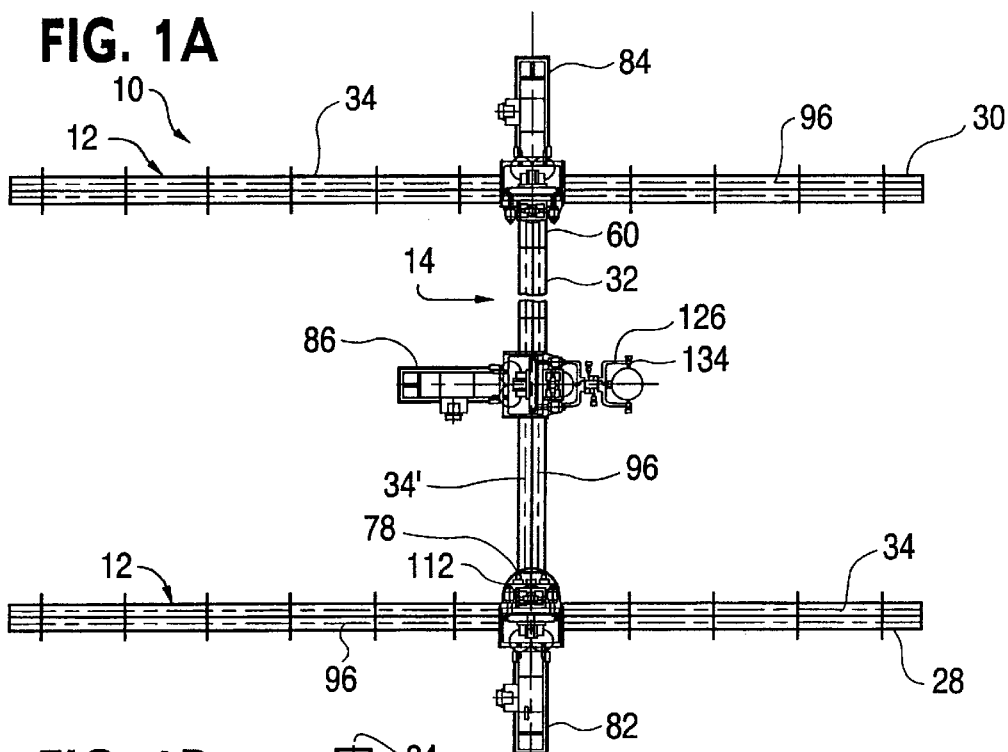
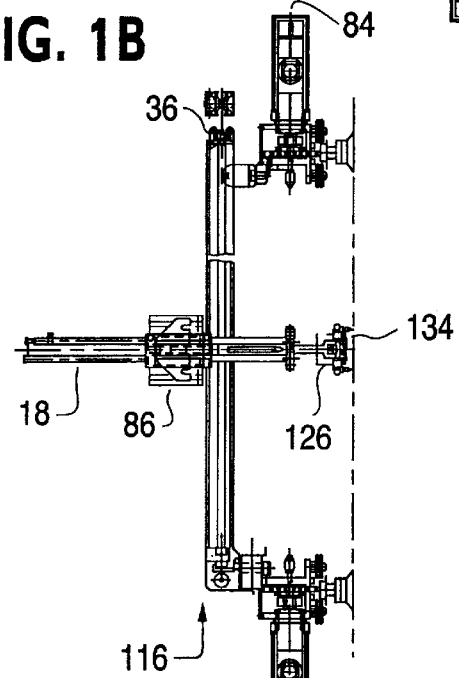
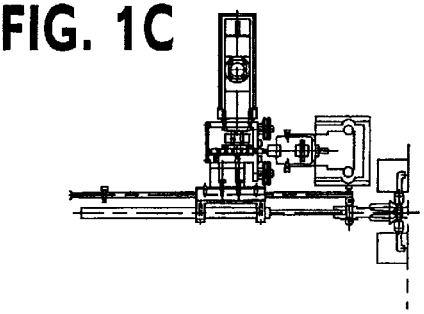
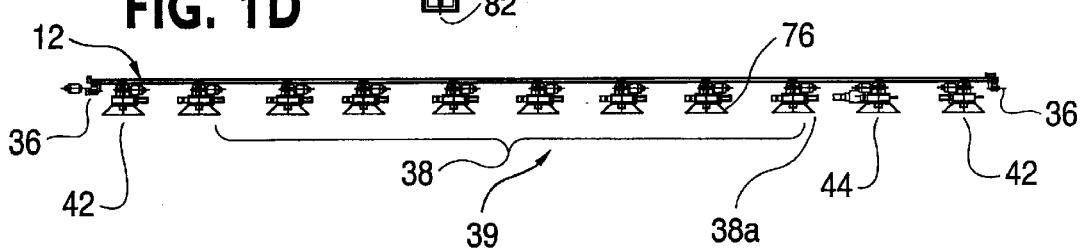

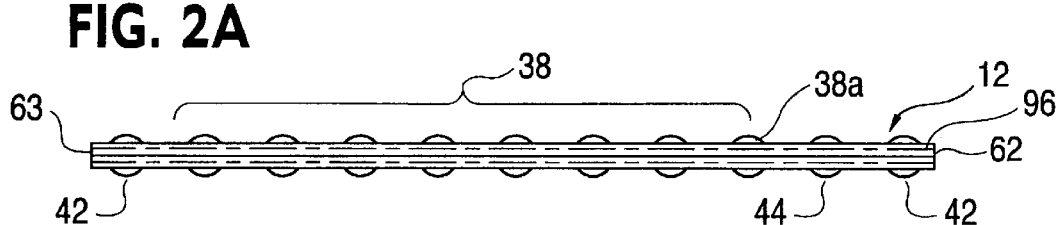
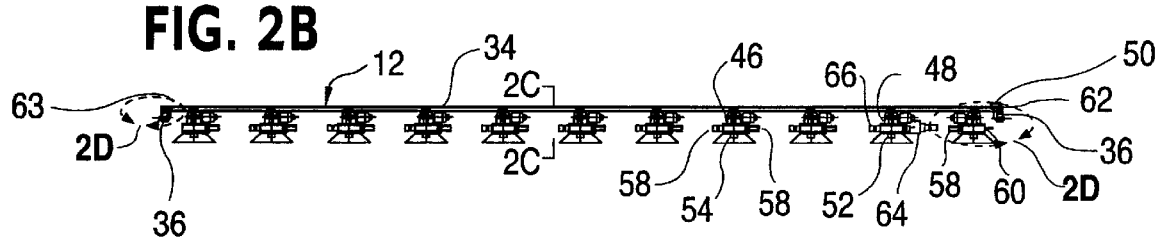
 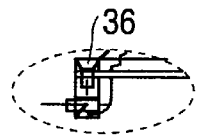 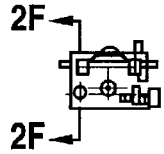 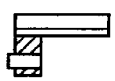
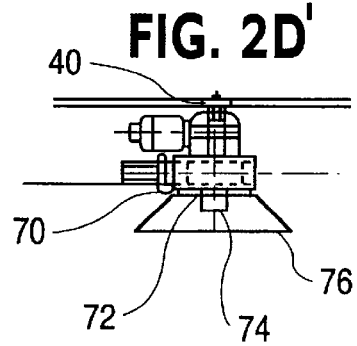
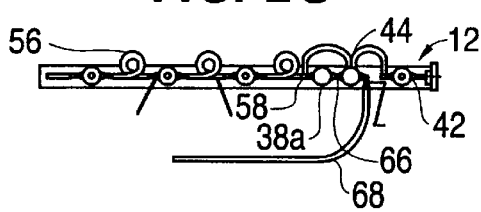 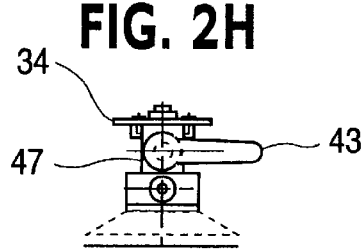

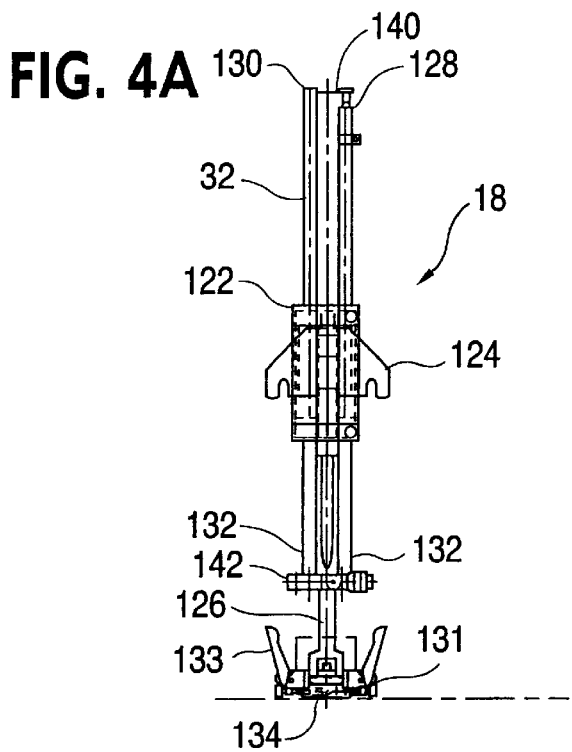
FIG. 4A
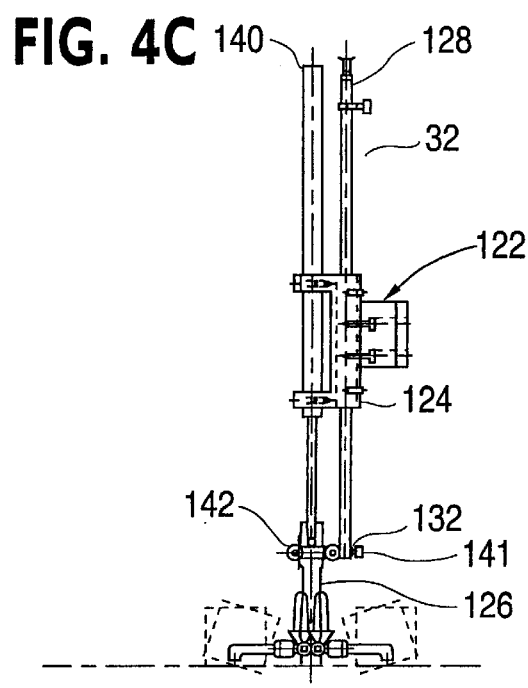
FIG. 4C
FIG. 4B
FIG. 4D
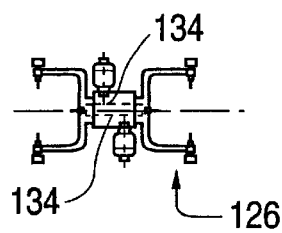
FIG. 4E
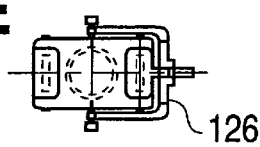
FIG. 4F
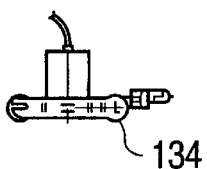
FIG. 4I
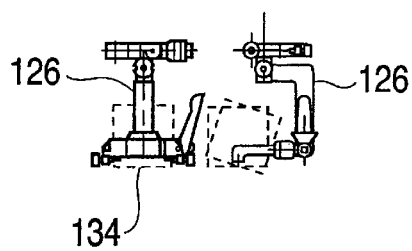
FIG. 4G
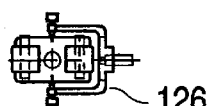
FIG. 4H
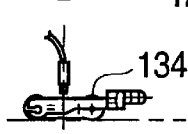
FIG. 4J
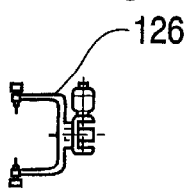

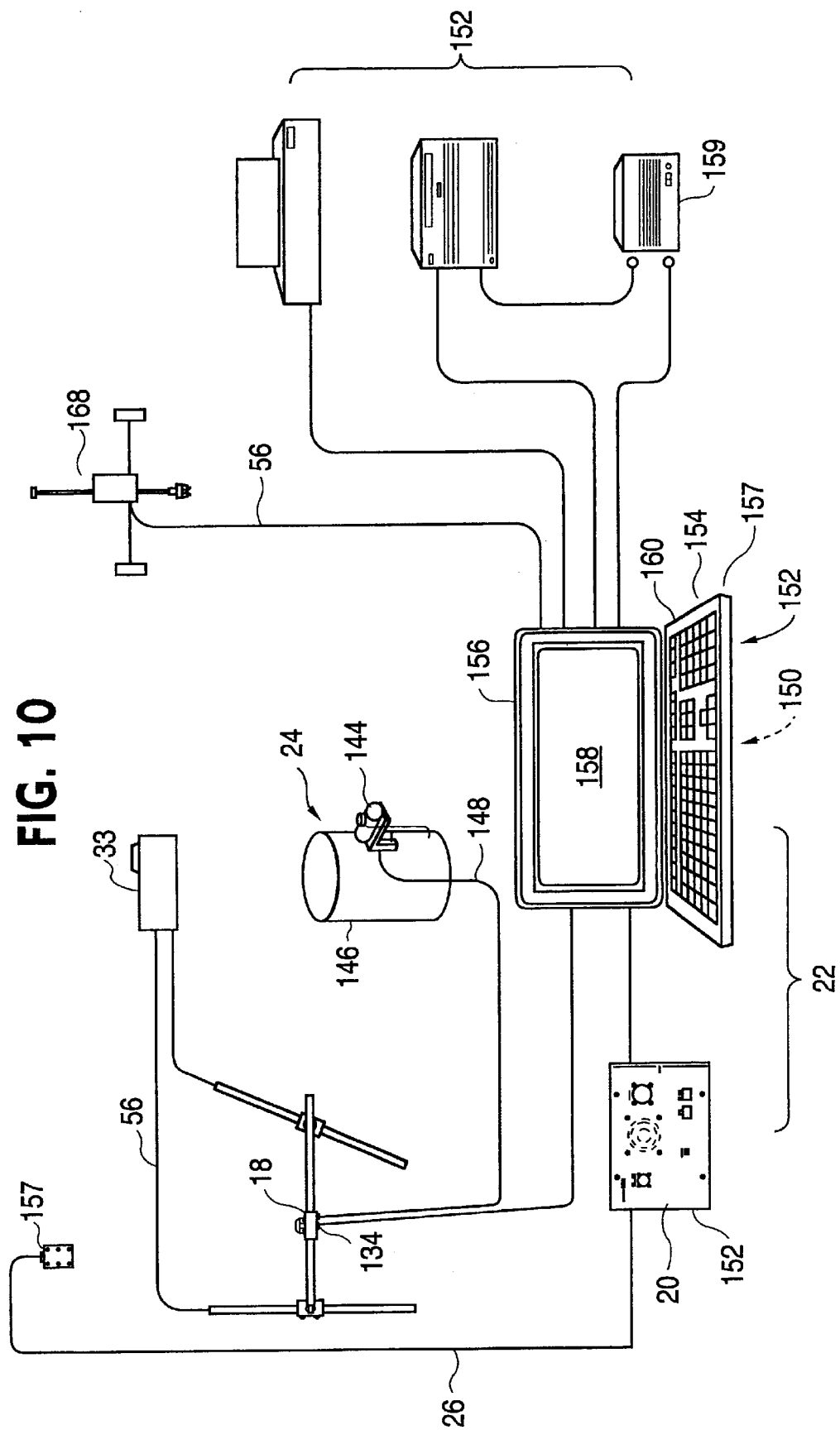

APPARATUS AND METHOD FOR PERFORMING NON-DESTRUCTIVE INSPECTIONS OF LARGE AREA AIRCRAFT STRUCTURES

CROSS REFERENCE TO RELATED APPLICATIONS

This application is related to and claims the benefit of U.S. Provisional Application No. 60/074,876, filed Feb. 17, 1998 and assigned to the assignee of the application.

FIELD OF THE INVENTION

This invention relates generally to machines for performing non-destructive inspections of large area aircraft structures. More particularly, this invention relates to an aircraft scanner having tracks secured to a surface of a large object, such as an aircraft. Still more particularly, this invention relates to a method and apparatus for manipulating a test probe in a rectilinear scan pattern with a master X-axis, a slave X-axis, and a Y-axis.

BACKGROUND OF THE INVENTION

Multi-axis robotic manipulators, also know as mechanical scanners, are used for performing non-destructive inspections (NDI) of materials in many industries. The designs of such machines vary widely and include X-Y gantry systems, X-Y manipulators, R-THETA manipulators, and Z-THETA manipulators. While the specific designs of such machines vary widely, their theories of operation are similar. Mechanical scanners are used to manipulate a NDI probe in a pre-programmed scan pattern on an inspection surface. An analog signal from the NDI probe is monitored, digitized, and displayed by a data acquisition and analysis system. Position information provided by feedback devices on the scanner is used by the data acquisition and analysis system to develop a two- or three-axis mapping of the NDI information. Typical NDI methods used with this type of machine include ultrasonic testing, eddy current testing, and mechanical impedance testing.

Non-destructive inspections of military and civilian aircraft are currently being performed at various maintenance facilities throughout the United States. Ultrasonic methods and mechanical impedance methods are commonly used to detect disbonds between the outer skin and the honeycomb core in composite aircraft structures such as wings. Such disbonds may be caused by repeated stress reversals or water entrapment within the structures. Eddy current methods are currently being used to detect surface cracking in thin skin aircraft structures such as fuselages. Cracks in the skin commonly develop around fasteners and are caused by repeated stress reversals within the structures.

Most of the NDI of modern aircraft is being performed using manual techniques. These techniques require that a technician manipulate a hand-held probe on the aircraft surface while simultaneously monitoring a NDI instrument. Thus, the quality of manual NDI techniques is highly operator dependent. Moreover, such manual NDI techniques are labor intensive and slow. Still further, NDI data obtained during manual inspections cannot, in general, be saved as a permanent record.

NDI of modern aircraft is currently being performed using a limited amount of automated NDI techniques. Growth in the use of automated NDI methods has been limited due to the complex nature of modern aircraft structures. Typical aircraft surface geometries may be flat, conical, cylindrical, or some combination of the three representative typical surface geometries. The surface curvatures may be convex or concave, while the surface orientations may be horizontal, vertical, or overhead.

Most on-aircraft automated NDI techniques require the use of a mechanical scanner to manipulate a NDI probe, whether ultrasonic, eddy current, or mechanical impedance, in a preprogrammed scan pattern on the aircraft surface. Various aircraft scanner designs exist. These designs include rigid X-Y gantry systems which are supported by floor-mounted bases or which are mounted to the aircraft surface by vacuum cups. Another common design involves the use of a track-mounted, two-axis scanner. In this type of system, a vacuum track is coupled to the surface of the aircraft structure. A two-axis scanner mounts to the vacuum track via guide rollers or magnetic wheels. The X-axis typically coincides with the track axis. A cantilevered Y-axis is oriented 90 degrees relative to the X-axis.

Conventional mechanical scanner designs have seen limited use in aircraft NDI applications because they are not well-suited to the demands of the task. Conventional gantry systems are well-suited for inspecting large areas with flat surfaces but they cannot be adapted conveniently for small diameter curved surfaces or areas with limited access. Conventional vacuum track-mounted scanners can adapt to both flat and curved surfaces, but they can only cover a narrow area due to the cantilevered Y-axis.

Accordingly, a need has been recognized for a mechanical scanner which can be used to perform non-destructive inspections of large area aircraft structures, which can conform to the complex surface curvatures present on modern aircraft, and which is lightweight, less expensive, and has improved speed capabilities and enhanced flexibility in relation to existing designs.

SUMMARY OF THE INVENTION

Directed to achieving the foregoing and additional objectives and overcoming shortcomings of the prior art systems, a main object of the invention is to provide a scanner which efficiently performs non-destructive inspections of large area aircraft structures.

Another object of the invention is to provide a scanner according to the invention which interfaces to ultrasonic, eddy current, and mechanical impedance NDI probes.

Another object of the invention is to provide a scanner which manipulates a NDI probe in a rectilinear scan pattern when operated under control of a motion control system.

Still another object of the invention is to provide a scanner which conforms to complex surface geometries present on modern aircraft, these surface geometries include flat surfaces, convex curved surfaces, concave curved surfaces, cylindrical surfaces, conical surfaces, and parabolic surfaces.

Another object of the invention is to provide a scanner which operates on horizontal, overhead, and inverted aircraft structures.

A yet further object of the invention is to provide a scanner which couples to aircraft surfaces via an array of vacuum cups.

Still another object of the invention is to provide a scanner which is lightweight, portable, and easily set up by a single operator.

Another object of the invention is to provide a scanner which uses a modular design to facilitate equipment set up on the aircraft.

Another object of the invention is to provide a scanner which combines the large area inspection capabilities of a two-axis gantry system with surface-following and contour-following capabilities of a two-axis track-mounted scanner.

The foregoing and other objects of the present invention are accomplished by providing a scanner with two flexible tracks. Each flexible track is fitted with a motor driven tractor assembly. A rigid beam track spans the two flexible tracks. The rigid beam track spans between the two flexible tracks, and is coupled to each tractor assembly by articulating joints. The articulating joints permit movement at the joints along at least three independent axes.

The rigid beam supports a third motorized tractor. This third tractor supports a compliant thruster assembly that deploys gimbaled mechanical impedance, ultrasonic or eddy current inspection probes. The gimbal positively loads the inspection probes, keeping them in contact with the inspection surface with near constant force.

The rigid beam track serves as the scanner's Y axis. The flexible vacuum tracks serve as the X axis. The Y axis stroke is limited to the length of the rigid beam. The X axis stroke can be made infinitely long by connecting multiple track sections in a chain.

The scanner also includes a data acquisition and analysis system that controls scanner functions and operations. The movement of the scanner is controlled by a scan control subsystem forming part of the data acquisition and analysis system. The scan control system includes both hardware and software for controlling the movement of the scanner over the surface to be inspected. The software includes a teach mode that permits an operator to preprogram the scan pattern for the surface to be inspected using a global coordinate system. The global coordinate system allows the operator to reference points on the surface and the data display using an identical coordinate system.

The scanner may be used to inspect surfaces including complex geometrical shapes. The scanner is particularly adapted for use in inspecting horizontal, overhead, and inverted aircraft surfaces.

BRIEF DESCRIPTION OF THE DRAWINGS

The features and inventive aspects of the present invention will become more apparent upon reading the following detailed description, claims and drawings, of which the following is a brief description:

FIGS. 1A–1D show views of the flexible configuration of the scanner according to the invention, in which FIG. 1A is a top plan view of an assembly of a Y-axis track assembly, an X-axis flexible track assembly, a master X-axis tractor assembly, a Y-axis tractor assembly, a slave X-axis tractor assembly, and a thruster assembly;

FIG. 1B is a side elevational view of the assembly of FIG. 1A, and

FIG. 1C is an end view of the side view of FIG. 1B, and

FIG. 1D is a side elevational view of the assembly of FIG. 1A.

FIGS. 2A–2H show views of of a flexible track assembly for the scanner according to the invention, in which FIG. 2A is a top plan view of a track used in the invention;

FIG. 2B is a side elevational view of the track shown in FIG. 2A;

FIG. 2C is a cross-section taken along line B—B of FIG. 2B;

FIG. 2D are receptively details of the ends of the track shown in FIG. 2B;

FIG. 2E is an end view of the track shown in FIGS. 2B and 2D;

FIG. 2F is a cross-section taken along line A—A of FIG. 2E;

FIG. 2G is a plan view of the flexible track assembly with a flexible vacuum line; and FIG. 2H is a detailed view of the right end of the track of FIG. 2B.

FIGS. 3A–3E are assembly drawing of a Y-axis track assembly for the scanner according to the invention, in which FIG. 3A is a side view of the Y-axis track assembly;

FIG. 3B is a plan view of the Y-axis track assembly according to FIG. 3A;

FIG. 3C is a cross-section view taken along line D—D of FIG. 3B;

FIG. 3D is a detailed view of one end of the track assembly shown in FIG. 3A; and FIG. 3E is an expanded view of the other end of FIG. 3A, including an expanded end view of that same end.

FIGS. 4A–4J are assembly drawings of the thruster assembly shown in FIG. 1 for the scanner according to the invention, in which FIG. 4A is a plan view of the thruster assembly, FIG. 4B is an end elevational view of the end of the assembly of FIG. 4A;

FIG. 4C is a side elevational view of the thruster assembly of FIG. 4A;

FIG. 4D is an end view of an end of the thruster assembly shown in FIG. 4C;

FIG. 4E is a plan view of an optional sled assembly for use with the thruster assembly;

FIG. 4F is a side elevational view of the probe sled assembly of FIG. 4E;

FIG. 4G is a plan view of another probe sled assembly for use with the thruster assembly;

FIG. 4H is a side elevational view of the probe sled assembly of FIG. 4G;

FIG. 4I is a side elevational view of an optional single transducer setup for use with the thruster assembly of FIG. 4; and FIG. 4J is a side view of the transducer setup of FIG. 4I.

FIGS. 5A–5D are drawings is a drawing of a master X-axis tractor assembly shown in item 3 of FIG. 1, in which FIG. 5A is a top plan view of the subject assembly;

FIG. 5B is a side view, partially in section, of the subject assembly in FIG. 5;

FIG. 5C is an end elevational view of the assembly shown in FIG. 5A; and

FIG. 5D is a wiring diagram for connection the motor and optical encoder shown in FIGS. 5A and 5B.

FIGS. 6A–6D are assembly drawings of the slave X-axis tractor assembly for the scanner according to the invention, in which FIG. 6A is a top view of the subject assembly;

FIG. 6B is a side view, partially in section, for the assembly shown in FIG. 6A, FIG. 6C is an end view of the assembly shown in FIG. 6A; and FIG. 6D is a wiring diagram for connecting the motor and encoder as shown in FIGS. 6A and 6B.

FIGS. 7A–7D are assembly drawings of the Y-axis tractor assembly of FIG. 1 in which FIG. 7A is a top view of the subject assembly;

FIG. 7B is a side view, partially in section, for the assembly shown in FIG. 7A;

FIG. 7C is an end view of the assembly shown in FIG. 7A; and

FIG. 7D is a wiring diagram for connecting the motor and encoder as shown in FIGS. 7A and 7B.

FIG. 10 is a system diagram of the scanner of FIG. 1 showing the interrelation of major system components

DESCRIPTION OF THE PREFERRED EMBODIMENT

Figure 3A:
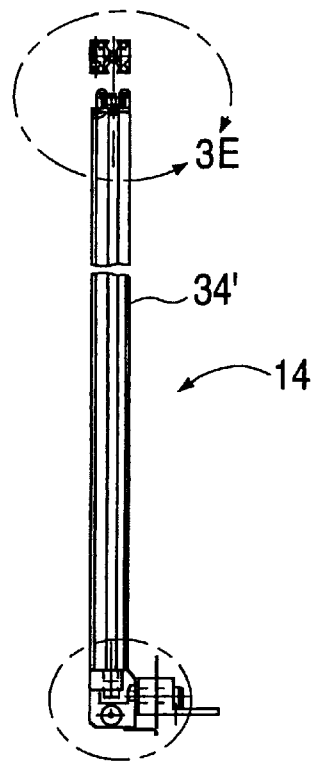
Figure 3B:
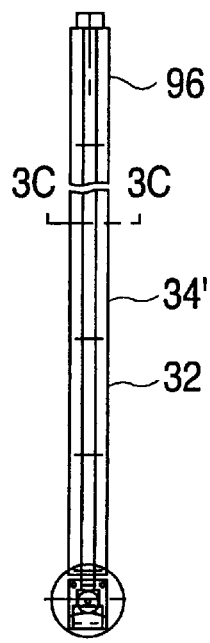
Figure 3C:
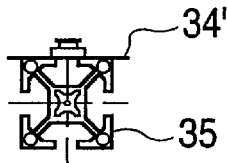
Figure 3D:
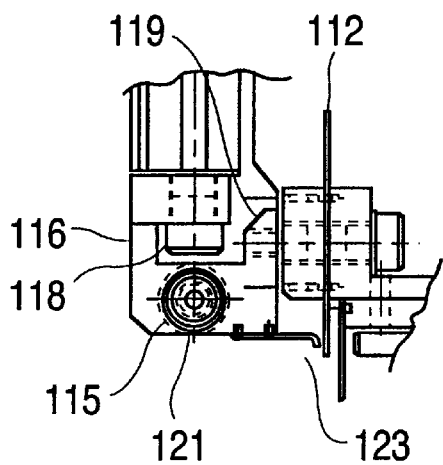
Figure 3E:
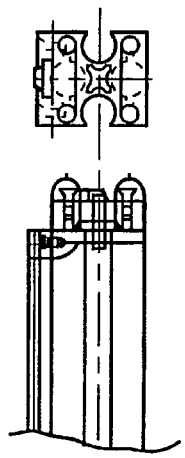

The scanner 10 enables an operator to perform nondestructive inspection (NDI) of a wide variety of surface types. The scanner 10 shown in FIGS. 1–10 includes three interrelated track assemblies. These track assemblies separately include several common elements. It will be understood that common reference numerals are used to describe common features of the embodiment of the scanner shown in FIGS. 1–10.

FIG. 1 shows a scanner 10 formed according to the present invention. The scanner 10 includes a vacuum track assembly 12, a Y-axis track assembly 14, a tractor assembly 16, a thruster assembly 18, a scan control subsystem 20, a data acquisition and analysis system 22, a couplant supply system 24, a vacuum supply system 33, and an umbilical cable assembly 26. To prevent damage to the identified components, the scanner 10 may be tethered to an external device to prevent the scanner 10 from falling should it become detached from the inspection surface. The exposed components of the aircraft scanner 10 are fabricated of a corrosion resistant material or are adequately corrosion protected. However, it will be appreciated that other materials may be selected.

The vacuum track system 12 couples the scanner 10 to the surface to be inspected. As illustrated in FIG. 2, the vacuum track system 12 includes a master X-axis vacuum track assembly 28 and a slave X-axis vacuum track assembly 30. It will be understood that the X- and Y-axes orientations refer to the generally known X-Y coordinate system. However, the track assemblies 28, 30 and 32 (discussed below) are designed to permit various angular and linear orientations relative to the X-Y coordinates of the surface to be inspected. For instance, in one embodiment of the scanner 10, the master X-axis assembly 28 and the slave X-axis track assembly 30 are spaced apart in a vertical orientation. As the X-axes track assemblies 28, 30 are configured in a master-slave relationship, the lengths of the X-axes vacuum track assemblies 28, 30 do not have to be in parallel alignment.

It will be appreciated that the master X-axis 28 and the slave X-axis 30 each include common features, and thus are discussed jointly using common reference numerals to describe common features. The X-axes vacuum track assemblies 28, 30 each includes at least one track plate 34 section, which forms the primary support surface for the vacuum track assemblies 28, 30, and an array of vacuum cups 39, and an end of travel hard stop mechanism 36.

The track plates 34 can be used singly or interconnected as discussed above. An indefinite number of track plate 34 sections may be coupled together to form the desired track length. The track plates 34 have an overall length of four feet, and are fabricated using a thin gauge spring steel. It will be appreciated that various lengths and other appropriate materials may be used. The flexible track plates 34 do not yield or plastically deform upon bending and twisting, if necessary, to adapt the track plates 34 to the curvature of the surface to be inspected. The vacuum track plates 34 may be adjusted to mate with horizontal, vertical, overhead, conical, cylindrical, flat, concave, convex and compound curved surfaces or any combination of the aforementioned surfaces. In particular, the track plates 34 are especially adapted to conform to curved surfaces typically found on an aircraft fuselage, wing and engine support structures such as cowls.

The track plates 34 support an array of vacuum cups 39. The array of vacuum cups 39 includes a plurality of vacuum cup assemblies 38, at least two end vacuum cup assemblies 42, and at least one control vacuum cup assembly 44. The number of vacuum cup assemblies 38 used per unit track 28, 30 length varies depending on the size of the surface to be inspected and the number of track plates 34 needed. However, the number of vacuum cups 38 used should provide for a smooth track curve that approximates the curvature of the surface to be inspected.

The embodiment illustrated in FIG. 2 shows one end cup assembly 42 positioned on each end 62, 63 of the vacuum track assemblies 28, 30. Positioned between the two end cup assemblies is a plurality of vacuum cup assemblies 38. FIG. 2 also shows the control cup assembly 44 positioned on the track assembly 28, 30 between one end cup assembly 42 and the first vacuum cup assembly 38a.

Each vacuum cup assembly 38, 42 and 44 includes a housing 46, 47 and 48, respectively. A mechanical fastener such as a screw couples each housing 46, 47 and 48, respectively, to the track plate 34. Each housing 46, 47 and 48 supports a mounting hinge 40 for coupling each vacuum cup assembly 38, 42, and 44 to the respective housing 46, 47 and 48. The mounting hinge 40 permits positioning the vacuum cup assemblies 38, 42 and 44 at various angular orientations. Each housing 46, 47 and 48 also supports an adjustable handle 43 for positioning the vacuum cup mounting hinge 40 in the desired orientation.

This angular adjustment feature permits the X-axes vacuum track assemblies 28, 30 to be mounted onto conical or irregular surfaces as discussed above. In one embodiment, the mounting hinge 40 permits adjusting each vacuum cup assembly 38, 42 and 44 to an angular position between zero and thirty degrees relative to the respective vacuum track assembly 28, 30. It will be appreciated that other angular settings are possible. Such an adjustment permits the X-axes vacuum track assemblies 28, 30 to mate with surfaces having small diameters.

With respect to the vacuum cup assembly 38, the housing 46 defines an opening 54 extending therethrough. Each side of the opening 54 receives a barbed fitting 58 that extends outwardly from the opposite sides of the vacuum cup assembly 38. However, the opening 54 of the first vacuum cup 38a receives the barbed fitting 58 only in the portion of the opening 54 facing the array of vacuum cup assemblies 38. The opposite side of the opening 54 for the vacuum cup 38a receives a close nipple 66 that prevents air at ambient pressure from flowing into the vacuum cup 38a.

Each barbed fitting 58 supports a length of tubing 56. Together the tubing 56 and the vacuum cup assemblies 38, 42 and 44 create a pneumatic circuit such that the tubing 56 serially couples the vacuum cup assemblies 38, 42 and 44 to an external vacuum source 33 (discussed below). Specifically, the vacuum cup assemblies 38, 42, and 44 of each four-foot track plate 34 section are independently plumbed to the vacuum source 33. Consequently, a failure in one track plate 34 segment will not cause other segments to fail.

Turning now to the end cup assemblies 42, the housing 47 defines an opening 50. One side of the opening 50 receives the barbed fitting 58 and tube 56 assembly. A hex plug 60 caps the other side of the opening 50. At the end 63 of the track assembly 28, 30, the tubing 56 couples the end cup assembly 42 to an adjacent vacuum cup assembly 38. At the opposite end 62, the tubing 56 couples the other end cup assembly 42 to the control cup assembly 44.

With respect to the control cup 44, the housing 48 defines an opening 52. One side of the opening 52 receives an air valve 64 that couples the vacuum control cup 44 to a source of vacuum pressure via tubing 68. The other side of the opening 52 receives a close nipple 66 that prevents air at ambient pressure from entering the opening 52. Additionally, each housing 46, 47 and 48, respectively, supports a vacuum cup mounting bracket 70. The mounting bracket 70 supports a flexible cup-shaped vacuum pad 76. The vacuum pad 76 mechanically couples to the mounting bracket 70 using known techniques such as screw threads or other similar methods. Additionally, the mounting bracket 70 defines an opening 72. The opening 72 is in fluid communication with openings 54, 50 and 52, respectively, and is covered by an end cap 74.

The vacuum pad 76 surrounds the end cap 74, and provides a soft smooth surface that physically engages the surface to be inspected. For instance, when vacuum pressure is applied to the vacuum cup assemblies 38, 42 and 44, a suction force is induced through the end cap 74 into the open center formed by the vacuum pad 76. This force causes the vacuum pad 76 to adhere to the surface to be inspected.

The vacuum pressure applied to the vacuum pad 76 is sufficient to permit the vacuum cup assemblies 38, 42 and 44 to form leak proof seals with rough as well as smooth surfaces. It is possible, however, that the integrity of the surface may not permit a vacuum tight seal between the vacuum cup assemblies 38, 42 and 44 and the surface under inspection. Consequently, the leakage of up to two vacuum cup assemblies 38, 42 and 44 each four foot track plate 34 section generally does not affect overall vacuum track 28, 30 coupling to the surface being inspected. It will be appreciated, however, that the number of vacuum cups 38, 42 allowed to leak during the inspection process may vary depending on the size of the vacuum pump and cups used.

An electric vacuum pump (not shown) induces a vacuum pressure at the vacuum cup assemblies 38, 42 and 44. In one embodiment, the vacuum pump is rated for 110–120V AC power, and is rated for explosion proof service in accordance with the National Electric Code, Article 500, Class, Group D locations, said standard incorporated herein by reference. The pump has sufficient capacity to provide the required coupling force for both the master X-axis 28 and the slave X-axis 30 vacuum cup assemblies 38, 42 and 44.

In the event the vacuum tracks 28, 30 are too long for the surface to be inspected, the excess vacuum cups 38, 42 are capped using known techniques. To further facilitate single operator loading of the scanner 10 onto the surface to be inspected, an audible warning system (not shown) alerts the operator of possible vacuum cups 38, 42, 44 decoupling. The audible warning is activated upon detection of a partial loss of vacuum.

Finally, the X-axes vacuum track assemblies 28, 30 include an end of travel hard stop mechanism 36 supported by the distal ends 62, 63 of each vacuum track assembly 28, 30. The hard stop prevents the X-axes tractors 82, 84 (discussed below) from running off the ends of the tracks 28, 30. The motor current limits in the scan control subsystem 20 interrupt power if a tractor 82, 84 is driven into a hard stop 36.

Turning now to a description of the X-axes tractor assemblies 82, 84, as illustrated in FIGS. 5–6, each track assembly 28, 30 supports separate tractor assemblies 82, 84. Together, the master X-axis tractor 82/track 28 assembly, including one section of track 28, 30, inclusive of fixturing, position sensors, and drive components, form a lightweight assembly. Additionally, the X-axes tractors 82, 84 have an axis repeatability capability that permits certain locations to be returned to repeatedly with minimal error. Additionally, the X-axes tractors 82, 84 include axis position resolution capabilities.

Each tractor assembly 82, 84 includes a pinion gear 88, and a plurality of V-shaped guide rollers 90. In one embodiment, separate gear assemblies couple the respective tractor assemblies 82, 84 to the respective track assembly 28, 30. To that end, the track plate 34 receives and supports a lightweight gear rack 96. The gear rack 96 is bonded to the track plate 34 such that the gear contacting face of the gear rack 96 is oriented face-up on the top surface of the track plate 34.

The gear rack 96 is designed in accordance with conventional standards, and receives a pinion gear 88 supported by the tractor assembly 82, 84, respectively. Each pinion gear 88 engages the gear rack 96 of the respective vacuum tracks 28, 30, forming a slip-free drive engagement. This arrangement, thus, forms a rack and pinion drive system capable of precision movement and positioning.

To facilitate the achievement of the slip free drive arrangement, the pinion gear 88 is motor driven. The driving motor 92 is a DC servo gear motor that mechanically couples the pinion gear 88 using conventional techniques. In the disclosed embodiment, a motor can 100 supports the motor 92, and the motor 92 is rated for explosion proof service in accordance with the National Electric Code, Article 500, Class 1, Group D, said standard incorporated herein by reference, or optionally certified per ML-M-8609, incorporated herein by reference.

A housing 102 retains both the motor 92 and the supporting motor can 100. The exterior surface of the housing 102 supports a plurality of V-shaped guide rollers 90. The V-shaped contacting surface 98 of the guide rollers 90 engages the edges of the respective X-axes 28, 30 track plates 34 in a way that the respective track plates 34 act as linear guides and the V-shaped guide rollers 90 act as linear bearings that facilitate the movement of the tractor assemblies 82, 84 along the X-axes tracks 28, 30. Thus, this arrangement further enhances the slip-free mechanical engagement between the respective tractor assemblies 82, 84 and the track assemblies 28, 30.

The housing 102 also supports at least one clamping handle 104 on the housing's 102 exterior surface. The clamping handle 104 supports a threaded shaft 106. Each shaft 106 of the respective tractor assembly 82, 84 housing 102 is received by a threaded surface supported by each track assembly 28, 30. The shaft 106, manipulated by the clamping handle 104, thus couples the respective tractor assembly 82, 84 to the respective X-axes track assembly 28, 30.

The clamping handle 104 functions similarly to a screw; however, the clamping handle 104 may be adjusted without the use of a separate tool, e.g., a screwdriver. The clamping handle 104 thus permits quick connect/disconnect of the tractor assemblies 82, 84 to/from the respective track assembly 28, 30.

Figure 5A:
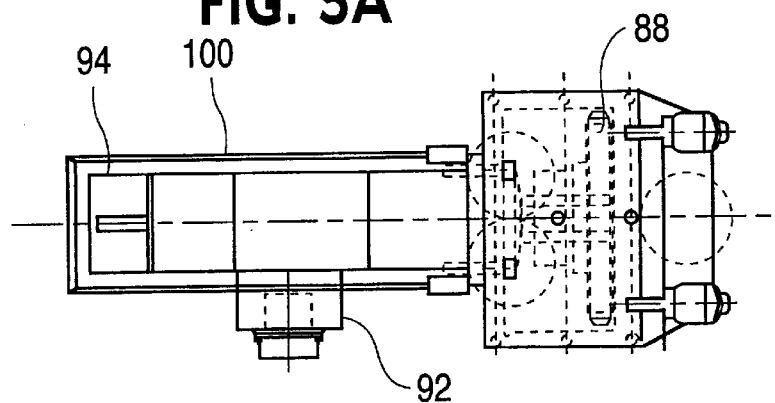
Figure 5B:
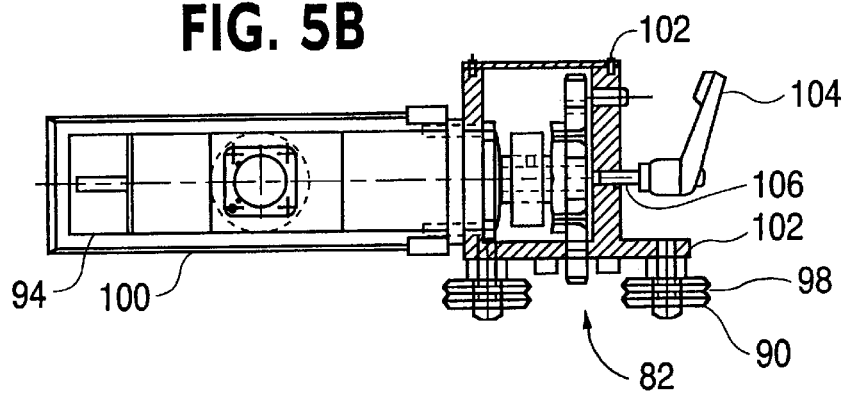
Figure 5C:
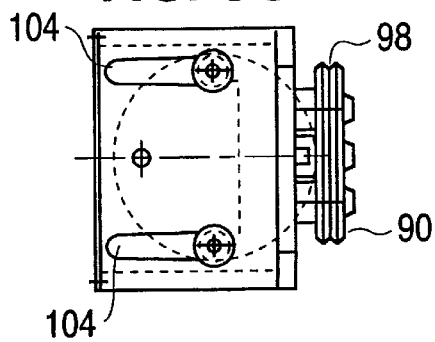
Figure 5D:
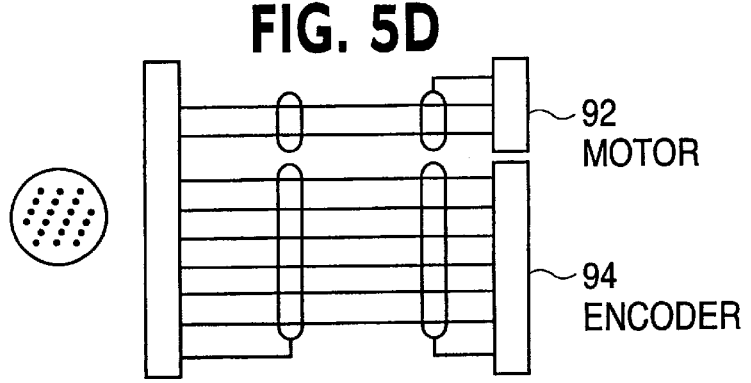
Figure 6A:
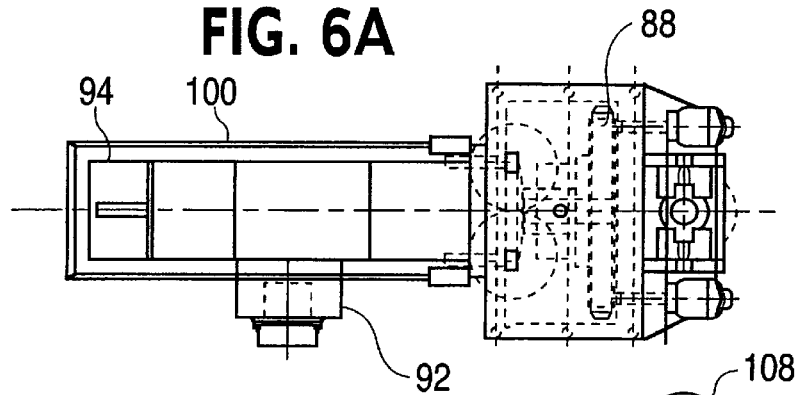
Figure 6B:
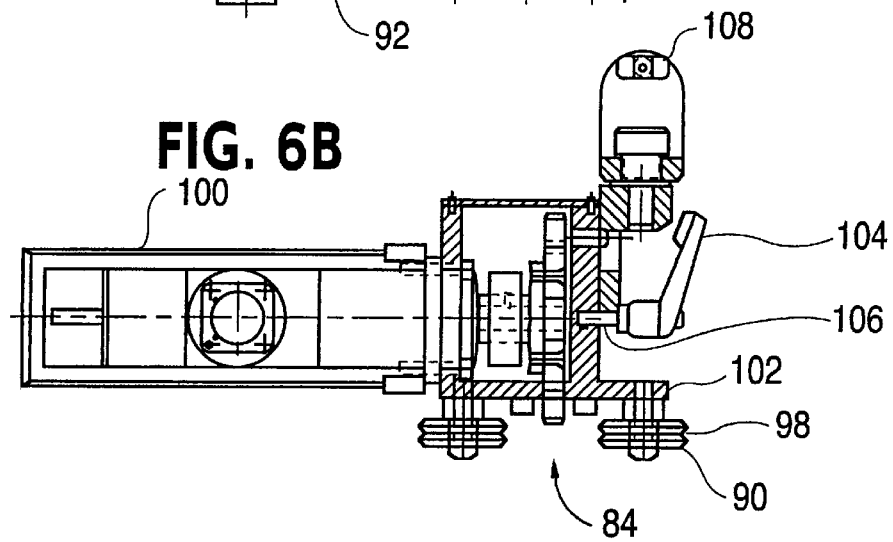
Figure 6C:
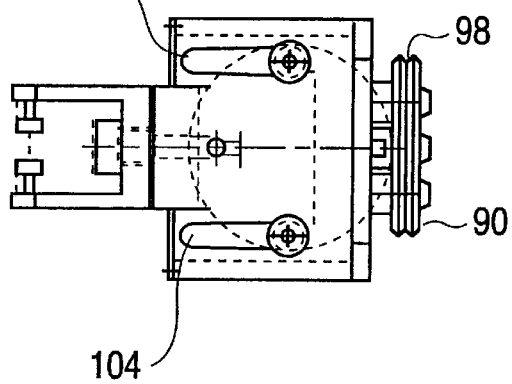
Figure 6D:
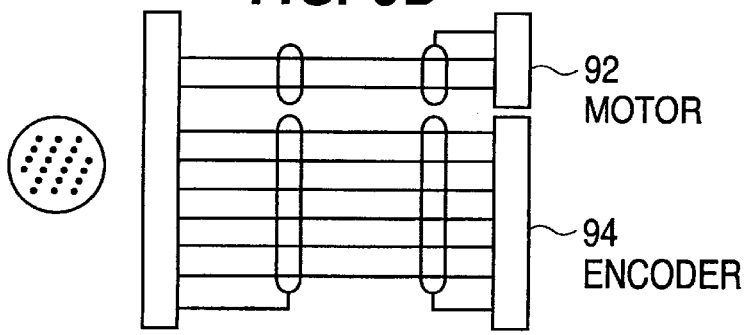
Figure 7A:
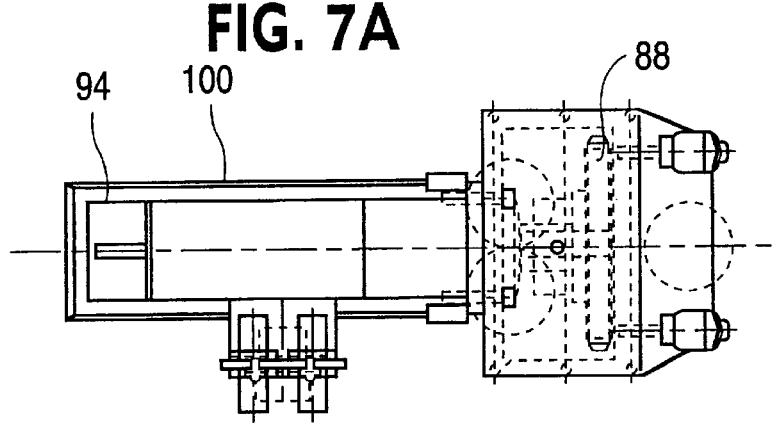
Figure 7B:
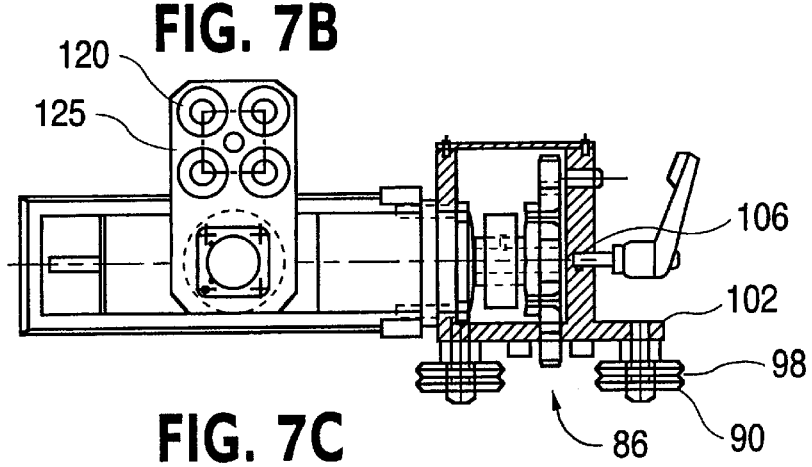
Figure 7C:
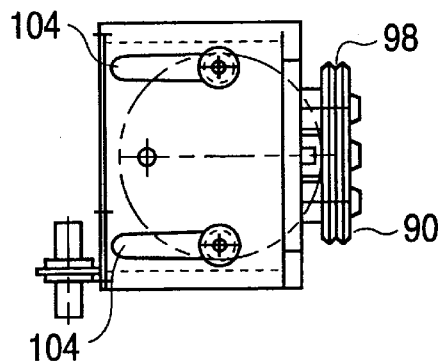
Figure 7D:
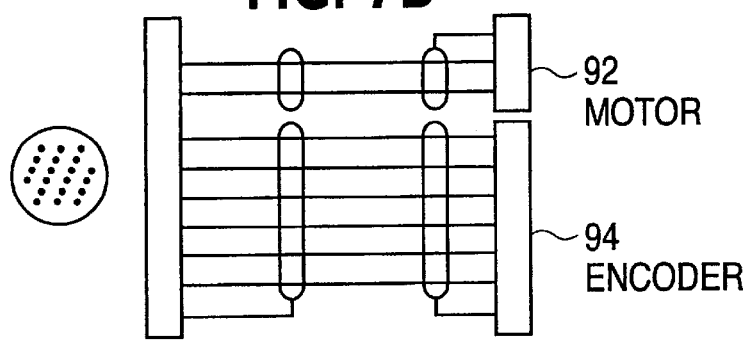

To aid in determining the accuracy of the selected location, each tractor assembly 82, 84 includes at least one optical encoder 94 for position feedback accuracy. As shown in FIGS. 5D and 6D, the motor 92 and the encoder 94 are electrically wired using standard wiring techniques.

In addition to the aforementioned components, the slave X-axis tractor assembly 84 includes a position adjustment mechanism 108. The position adjustment mechanism 108 through appropriate mechanical fixturing is coupled to the housing 102. As illustrated in FIG. 6, slide bearing pin screws may be used in coupling the position adjustment mechanism 108 to the Y-axis track assembly 32. Together, this coupling arrangement and the position adjustment mechanism 108 permit the slave X-axis 30 to move along three axes relative to the Y-axis 32.

Turning now to FIG. 3, the Y-axis track assembly 14 is shown. It will be appreciated that the Y-axis track assembly 14 and the X-axis track assembly 12 share common elements. Thus, common reference numerals are used to describe the common features. The flexible track assembly 14 includes at least one track plate 34', a rigid strut 35, an angle dial plate 112, and a master mounting bracket 116. The track plate 34' is fabricated of a flexible material such as spring steel. However, it will be apparent that the choice of material may vary depending on the desired level of flexibility. The track plate 34' is coupled to the rigid strut 35 by mechanical fasteners such as screws.

Figure 8:
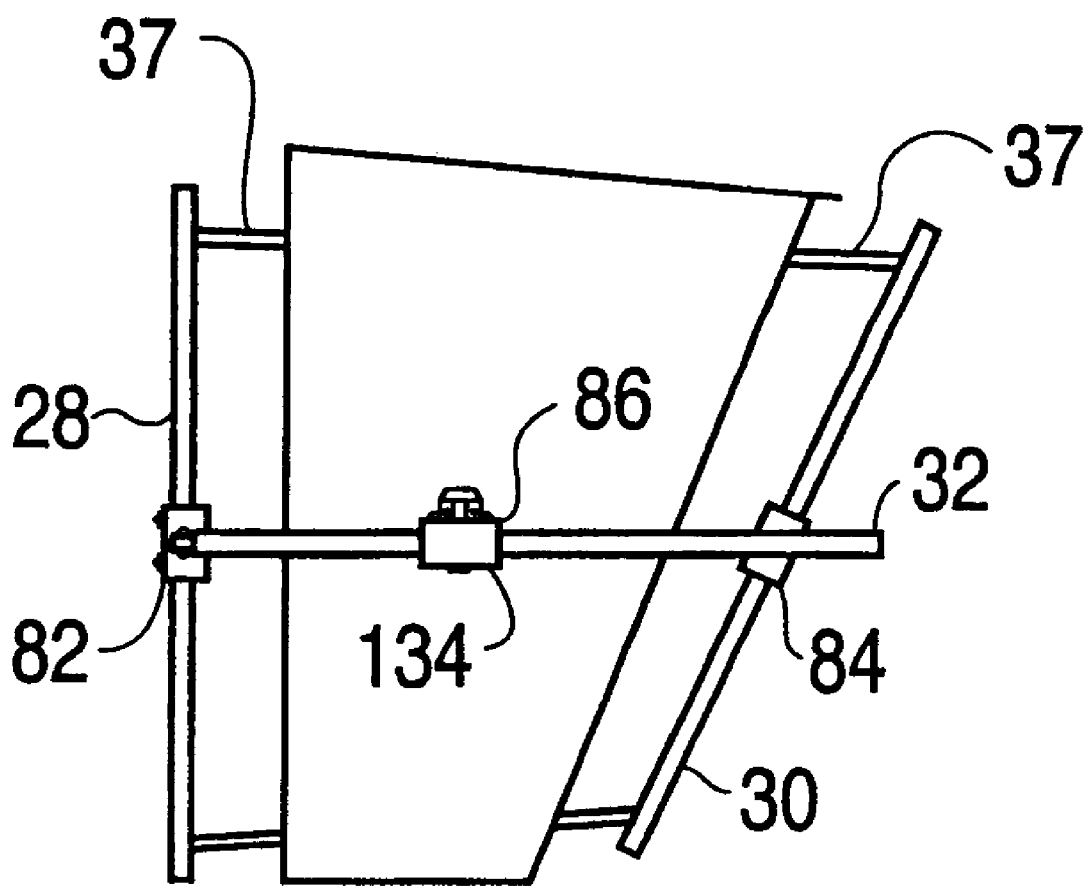
FIG. 8 is an assembly drawing of the scanner of FIG. 1 showing the master and slave X-axes offset by surface fixturing.
Figure 9:
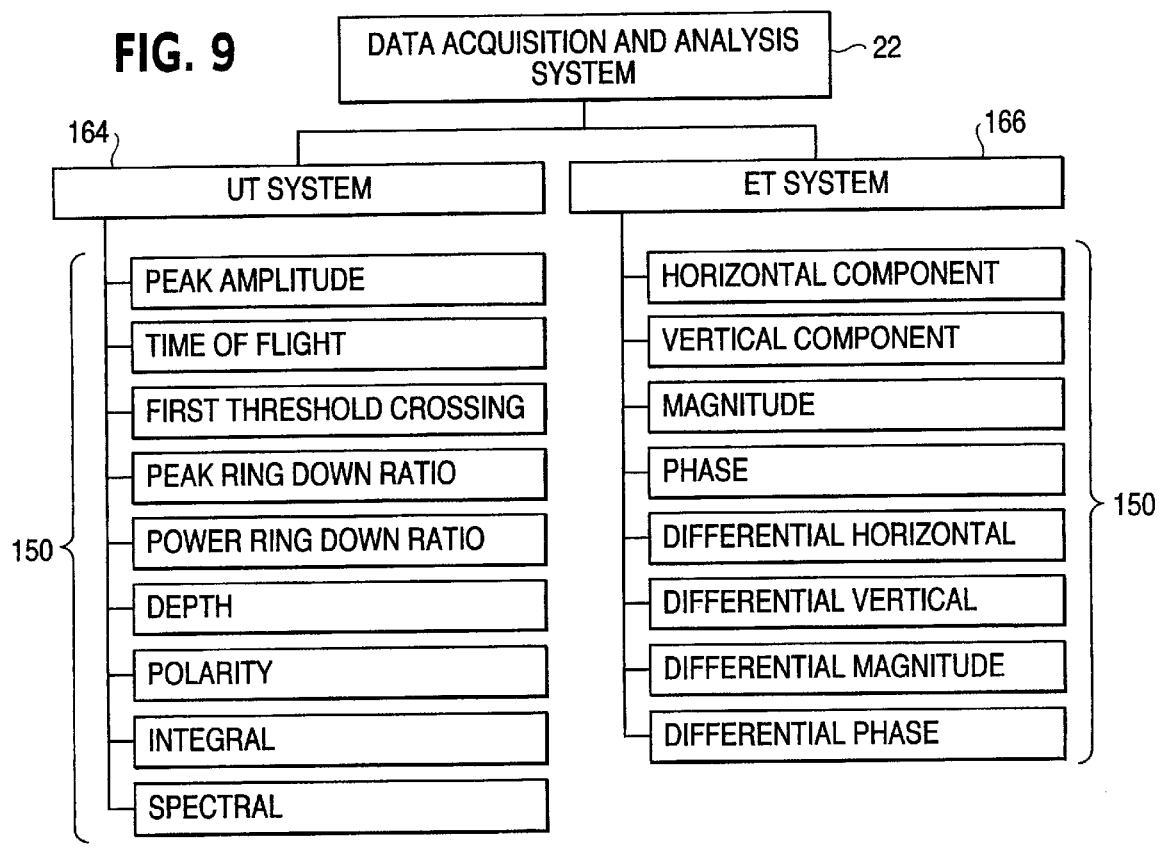
FIG. 9 is a block diagram of the scanner of FIG. 1 showing the analysis and software features of the data acquisition and analysis system.

The Y-axis track assembly 32 has a linear stroke of six feet. However, shorter track lengths may be used, particularly for scanning in confined areas. When assembled as a unit, the track assemblies 28, 30 and 32 permit scanning the surface under inspection to the track edges. To facilitate scanning up the partedges, vacuum coupled fixturing 37, as shown in FIG. 8, offsets the master and slave X-axes 28, 32 from the edges of the surface to be inspected.

As shown in FIGS. 1 and 3, the Y-axis track assembly 32 extends between the master X-axis track assembly 28 and the slave X-axis track assembly 30 such that the master X-axis tractor assembly 82 supports one end 78 of the Y-axis track assembly 32 and the slave X-axis tractor assembly 84 supports the opposite end 80. Additionally, the Y-axis track assembly 32 may overhang the X-axes tracks 28, 32. The Y-axis track assembly 32 need not extend perpendicularly to the X-axes 28, 30, particularly since the articulating joints coupling the Y-axis track assembly 32 and the X-axes tracks 28, 30 include multiple degrees of freedom.

The articulating joints accommodate non-parallelism and twist of the X-axes vacuum track assemblies 28, 30. Such an arrangement permits adjustment of the track assemblies 28, 30 and 32 to mate with surfaces of various configurations. In one embodiment, the articulating joints permit movement of the X-axes 28, 30 and the Y-axis 32 along three axes: altitude, azimuth and twist. These articulating joints may be established using appropriate quick connect/disconnect couplers and fasteners.

To accommodate movement along the three axes of movement, the end 78 supports a master mounting bracket 116 that supports an angle dial plate 112 and a pivot mechanism 115. The angle dial plate 112 is marked in gradients ranging from zero to 360 degrees. The angle dial plate 112 may be rotated to the desired angular position, and an indicator 123 visually marks the selected position. Thus, the angle dial plate 112 permits adjustment of the angular orientation of both the Y-axis track assembly 32 relative to the master X-axis assembly 28, as the master mounting bracket 116 supports both the Y-axis track 32 and the master X-axis track 28.

The Y-axis track assembly 32 and the master X-axis track assembly 28 are supported by the pivot mechanism 115 of the master mounting bracket 116. The pivot mechanism 115 is a U-shaped member forming an upper pivot block 118 and a lower pivot block 119. A bushing 121 supported by the pivot mechanism 115 permits slight movement of both the upper and lower pivot blocks 118, 119. Consequently, rotating the dial plate 112 causes movement of the upper and lower pivot blocks 118, 119, thus resulting in a relative change in position of both the Y-axis track assembly 32 and the master X-axis track assembly 28, respectively.

The Y-axis track 32 supports a gear rack 96 for receiving a pinion gear 88 supported by the Y-axis tractor assembly 86. This arrangement forms a rack and pinion arrangement, as described above for the X-axes tractor assemblies 82, 84. Except as otherwise specified, the Y-axis tractor assembly 86, shown in FIG. 7, includes each component previously described for the X-axes tractor assemblies 82, 84. Consequently, the previous discussion of the X-axes tractor assemblies 82, 84 sufficiently describes the components and general function of the Y-axis tractor 86.

In addition to the aforementioned components, the Y-axis tractor assembly 86 includes a BNC connector array 120. A plate 125 carried by the motor can 100 supports the BNC connector array 120, and the connectors are bulkhead BNC connectors.

As shown in FIGS. 1 and 4, the Y-axis track 32/tractor 86 assembly support a thruster assembly 18., A thruster bracket 122 couples the thruster assembly 18 to the Y-axis track 32/tractor 86 assembly using mechanical fasteners. The thruster assembly 18 may be placed on either side of the Y-axis track assembly 32.

The thruster bracket 122 supports a thruster slide block 124 and a gimbal 126. The thruster slide block 124 permits the thruster assembly 18 to move along the Y-axis track 32. Two shafts 128, 130 movably support the thruster slide block 124. The shafts 128, 130 extend in the same direction, and provide the surface over which the thruster slide block 124 travels.

The proximate end 132 of the shafts 128, 130 support the gimbal 126, which supports the nondestructive inspection (NDI) probes 134 that actually scan the surface to be inspected. The gimbal 126 extends outwardly from shafts 128, 130, and possesses at least two axes of movement. The gimbal 126 includes one or more outwardly extending prongs for supporting the NDI probes 134, which may or may not include probe sleds.

The gimbal 126 may be equipped with mechanical impedance, ultrasonic or eddy current NDI probes 134. For example, the NDI probes 134 may include a single transducer probe 134 as shown in FIGS. 4I and 4J, an ET probe sled assembly as shown in FIGS. 4G and 4H, or an ET probe sled assembly 138 as shown in FIGS. 4E and 4F. The transducer probes 134 used may include (1) one or two ultrasonic transducers with integral couplant feed; (2) one or two eddy current probes; or (3) one transducer with couplant feed and one eddy current probe.

The thruster assembly 18 provides for loading standard ultrasonic shear and longitudinal transducers having selectable crystal sizes appropriate to perform the function of the scanner 10, and eddy current surface probes with appropriate case diameters. It will be appreciated that other transducers and probes may be used. For instance, the gimbal 126 is capable of interfacing and scanning with other types of NDI probes such as those used in low frequency bond testing. However, care should be taken to maintain compatibility among the sensors, particularly with respect to length, diameter, and weight.

Clamping handles 131, 133 couple the NDI probes 134 to the gimbal 126. The clamping handle 131 permits adjustment of the angle of the NDI probe 134 along a 360° arc. The second handle 133 permits quick connect/disconnect of the coupling to the gimbal 126.

The gimbal 126 positively loads the NDI probes 134 to the surface under inspection. The positive load is provided by a gas spring 140. The gas spring 140 is of a conventional type, and applies a constant pressure to the end of the gimbal 126 to ensure full sensor contact with the surface under inspection.

The gas spring 140 provides a simple and effective means for facilitating movement of the NDI probes 134 smoothly over typical aircraft surfaces comprising multi-layer chipped paint, improperly installed countersink fasteners (which can be either protruding or recessed), skin dents, offset skin panels at interfaces and skin external repair doublers. The use of the gas spring 140 in conjunction with the disclosed gimbal 126 design dampens out possible NDI probe 134 oscillations as the probe traverses surface defects. In one embodiment, the constant pressure gas spring 140 helps the sensors negotiate abrupt offsets up to 0.125 inches.

An interface block 142 couples the shafts 128, 130 and the gas spring 140 to the gimbal 126. The interface block 142, thus, serves as a dampening mechanism. Additionally, the interface block 142 includes an clamping handle 141 having a threaded shaft that permits quick connect/disconnect coupling of the interface block to the end 132 of the shafts 128, 130.

The scanner 10 includes a portable couplant delivery system 24 for delivering coolant fluid to the ultrasonic probes during ultrasonic scanning operations. The primary couplant delivery 24 components include a delivery pump 144, couplant supply container 146, couplant filter (not shown) and required tubing 148. The delivery pump 144 directs couplant, water, from a supply tank 146 through tubing 148 and into irrigation ports leading to the ultrasonic transducer probes 134 on the scanner 10.

The delivery pump 144 provides a continuous, constant velocity couplant flow to the transducer 134 face. A variable speed drive motor powers the delivery pump 144. The drive motor is rated for explosion proof service in accordance with National Electric Code, Article 500, Class 1 Group D, incorporated herein by reference.

The filter removes particles that could reduce the performance of the ultrasonic inspection sequence. In one embodiment, the filter is supported by the inlet to the delivery pump 144 to prevent plugging of the delivery tubing and transducer 134 irrigation ports by dirt particles in the supply water. The filter provides for sufficient couplant flow throughout the operating period. However, the filter may need to be cleaned periodically to ensure efficient operation.

Control of couplant runoff is provided by passive hardware such as flexible strips or gutters. In a non-recirculating couplant delivery system 24, the flexible strips channel the majority of the spent couplant water from the inspection area by gravity via drain tubes into a collection container. However, if a recirculating system is used, the couplant is directed to the ultrasonic scanner probes using a closed-loop system, wherein the couplant is circulated back to the supply tank 146.

The tubing 148 used to connect the components of the couplant delivery system 24 is relatively flexible, and sized to deliver a sufficient amount of couplant fluid to the transducers 134. To that end, the couplant delivery system 24 is configured using known standards and techniques.

The analog signal from the NDI probes 134 is digitized and stored by an external data acquisition and analysis system 22. The data acquisition and analysis system 22 includes hardware and software subsystems 152, 150 for controlling scanner 10 operation.

The hardware subsystem 152 includes a portable computer 154 as the host computer. The computer 154 serves as the master computer for the scanner 10. An operator using a pointing device 157 such as a mouse or a keyboard 160 activates pull down menus, which are displayed on the computer screen 158. These menus include software files for controlling scanner 10 operations.

The computer 154 includes a CPU board including an Intel 486 DX2/66 MHz microprocessor and 64 Mb of RAM. The computer 154 is coupled to an uninterruptible power supply 159 that prevents the loss of data due to an AC power failure. When activated, the uninterruptible power supply 159 provides power to the computer 154 for a sufficient period of time to allow for a controlled shutdown of the computer 154.

The computer 154 also includes a ruggedized outer chassis 156 that encloses many components of the data acquisition and analysis system 22 hardware and software subsystems 152, 150 (discussed below).

The chassis 156 includes a fold-down front panel that includes a panel display 158 and a keyboard 160. The components forming the display unit include a VGA color display having a suitable resolution. For instance, the resolution may be 640×490 pixels. The display 158 is free from parallax and resolution/color fade when viewed at wide off-axis angles. The keyboard 160 is splash proof. As the keyboard 160 is included in the fold-down-front panel of the chassis 156, the keyboard 160 is up when not in use. The keyboard 160 forms part of the chassis 156 enclosure case, and provides protection for the panel display 158 when in the non-use position.

The chassis 156 also supports a pointing device 157. The pointing device 157 is a glidepoint-type structure for use with the graphical user interface. Additionally, the chassis 156 provides power to the axes of the scanner 10, and it supports connections for a joystick 157' for manual control and an emergency stop button. The chassis 156 also includes a port for connecting to an external VGA monitor, a minimum of one parallel port, two RS 232 ports, and at least one SCSI interface for data transfer and external data storage. The parallel port may be a Centronics port, and one serial port is dedicated to the pointing device. To facilitate data transfer, the chassis 156 supports hardware for modem or LAN data transfer. In one embodiment the modem has a 14.4K BAUD rate.

Additionally, the chassis 156 supports a data storage means. The data storage means includes an internal storage device such as RAM memory or an external device such as a floppy disk drive or a combination of an external storage device and an internal memory device, each having sufficient memory capacity to perform the NDI effectively. In one embodiment, the data acquisition and analysis system 22 includes a 1.44 Mb 3.5 floppy disk drive in combination with a 500 Mb internal hard drive, and an external 1 Gb read/write optical drive for system backup and permanent data storage and archival. It will be appreciated that the size of the data storage means may vary depending on system constraints.

The data acquisition and analysis system 22 can store the digitized RF waveform, peak and time-of-flight, and display the data along with the positional information. Stored data and processed information may be output using a printer 155 coupled to the host computer 154. One type of printer 155 that may be used is a Hewlett Packard™ 1200C color printer having at least 4 Mb RAM or equivalent.

Located within the computer 154 chassis 156 are additional components of the data acquisition and analysis system 22 hardware subsystem 152 (discussed below). Test parameters are programmed onto relevant hardware subsystem 152 components, and the programmed parameters control the scanning operation and the ultrasonic and eddy current subsystems.

One additional component of the hardware subsystem 152 is the scan control subsystem 20. The scan control subsystem 20 includes a multi-axis scan control board 162 and appropriate software (discussed below) for controlling the movement of the scanner 10. The scan control board 162 provides coordinated control of the movement of the scanner 10. The scan control board 162 has a master-slave capability that controls and monitors the X-axes tractor 82, 84 drive motors in a master-slave relationship. The scan control board 162 accepts download of scan parameters from the host computer 154 and provides the appropriate signal outputs to the respective DC servo motor 92 amplifier module. The signal output from the motor 92 amplifier module generates the correct drive voltages/current applied to each respective drive motor 92.

The motion control portion of the scan control subsystem 20 is configured on a daughter board of the data acquisition and analysis system 22. The corresponding servo amplifiers are mounted inside a separate electronics enclosure and electrically interfaced between the data acquisition and analysis system 22 and the scanner 10 with quick disconnect cables.

The scan control subsystem 20 operates in a closed loop format and is compatible with the data acquisition and analysis system's 22 ultrasonic pulse on position capability. Additionally, during data gathering or during post inspection data analysis, the scan control subsystem 20 causes the NDI probes 134 to traverse the surface under inspection using operator specified parameters.

During calibration, the operator uses the scan control system 20 to define the scan size, X and Y axes, and the scan grid resolution. As the scanner 10 can be used to inspect surfaces having various geometric configurations, the relative index/speed ratio between the master X-axis 28 and the slave X-axis 30 is variable and automatically determined during the teach mode (discussed below). The ratios established during the teach mode shall remain fixed during actual inspection scanning.

The operator enters the selected values directly or through a teach-and-learn technique. Using the teach-and-learn technique, the operator positions the scanner 10 at the starting point (0,0) and at each respective corner of a parallelogram, thus defining the overall scan area and shape. For example, during the teach-and-learn mode, the operator enters the global X-axis grid spacing and the global Y-axis grid spacing. The data acquisition and analysis system 22 then overlays onto the surface being inspected a global grid of the desired spacing and traverses the grid in 3-axes coordinated motion always staying on the global grid lines. Some benefits of this data recording method include:

C-scan displays that reflect true shape of scanned areas without pixel mapping losses that can be caused when attempting to display non-rectangular screen.

Data from the scans is rectilinear and in the same coordinate system so printouts are directly comparable.

Data from multiple scans is easily displayed in a merged display without data loss due to coordinate rotations.

For example, using the teach-and-learn technique of the present invention, the operator selects inspection area vertices defining the inspection area boundaries. The operator drives the NDI probe 134 to the scan start point, end point and required inspection area vertices using the joystick 157' or other device that provides for simultaneous axis 28, 30, and 32 movement. At each of these points/vertices, the operator enters the axis coordinates. Specific information entered by the operator includes the angle of the Y-axis track 32 relative to the master X-axis 28, the angle the master X-axis 28 makes relative to the global coordinate system reference point. The operator may also specify a target location and move the scanner 10 to that position, and assign a value to the scanner position. This feature allows the operator to reference the position encoder to the global coordinate system (discussed below).

The operator defines the common global coordinate system by identifying and selecting a local origin on the surface to be inspected. The global coordinate system, thus, provides reference to an identical coordinate system laid-out on the scanner 10 display 158. This enables the operator to determine the location of areas suspected of having defects in terms of the global coordinates of the scanned image or the global coordinates of the actual surface under inspection. Thus, the global coordinate system permits referencing points on the surface under inspection and the displayed image using an identical coordinate system.

Using the operator selected input, the scan control subsystem 20 manipulates the aircraft scanner over the surface, executing the taught, preprogrammed, scan pattern, and formulates the appropriate raster scan plan based on the operator selected maximum axis index distance (axes can index less than but never greater than this distance). The selectable maximum axis scan index distance is mapped out using appropriate increments. In one embodiment, the maximum axis scan index distance is set down to 0.005 inches in 0.005 inch increments or greater.

For instance, by employing the teach-and-learn technique, the scanner 10 is configured to scan complex geometrical shapes. For illustration purposes, the teach-and-learn will be explained for three and four sided polygons. These polygons may include interior angles ranging between 30 degrees and 150 degrees. Programming the scanner 10 to scan three sided polygons requires the operator to complete the following steps. First, the operator must define a global coordinate system (discussed below) from which other measurements are referenced. Second, the operator marks the form field "use global coordinate system" to TRUE, and enters on the form field the X and Y offset of the current scanner 10 origin relative to the global coordinate system. The operator also enters the angle of the scanner 10 master X-axis track 28 makes relative to the global coordinate system. Third, the operator enters the angle the Y-axis track 32 makes relative to the scanner 10 master X-axis track 28 for the first scan stroke. Fourth, the operator drives the scanner 10 using the joystick 157' to the scan starting location, local origin, and presses a button indicating to the system that this is the local origin. The X-axis and Y-axis encoder position is zeroed at this location. Fifth, the operator manipulates the scanner 10 using the joystick 157' so that the transducer 134 is at the end of the first stroke along the Y-axis track 32 and presses a button on the screen indicating the current position. The current Y-axis 32 position is read and used as the length of that side of the polygon. The slave X-axis 30 encoder is zeroed at this location. At this point, two sides of the desired polygon are known.

To measure four sided polygons, the operator drives the scanner 10 using the joystick 157' such that the transducer 134 is at the corner of the polygon opposite the local origin, and presses a button on the screen indicating that the scanner is at the third reference point. Each of the three axis positions is recorded. The information stored is sufficient to indicate two possible polygons. The shape used will be the polygon with an interior angle greater than 180 degrees.

If the joystick 157' is used during the teach-and-learn process, the joystick 157' is connected to the scanner end of an umbilical cable 26. The umbilical cable 26 connects the NDI probes 134 to the data acquisition and analysis system 22 and a servo amplifier chassis. The umbilical cable 26 assembly includes motor cables, encoder cable, joystick 157' cable, two RF ultrasonic cables, two RF eddy current cables, couplant delivery tubing, and a flexible fully zippered umbilical cable 26 outer jacket. The jacket II is made from a material that will not scratch or otherwise damage the surface under inspection.

In addition to the scan control board 162, the hardware subsystem 152 also includes an ultrasonic processor board 164, an eddy current processor board 166, and a video board. Board consolidation may be employed to reduce the number of boards used.

The ultrasonic board 164 is a multi-function board that includes an analog to digital (A/D) converter, a RF board, a video rectification board, a pulser receiver, a multiplexed ultrasonic receiver, digital amplitude correction (DAC), hardware gates, data compression, capabilities, video detection and run length encoding.

The analog to digital (A/D) portion of the ultrasonic board 164 operates at a user defined rate. In one embodiment, the rate may range between 1 and 100 MSPS, inclusive. The A/D conversion rate is selectable in distinct steps between 1 and 100 for convenience. For instance the rate may be selected in graduated steps, e.g., 5, 10, 15 SPS, etc. The A/D board also includes a sample memory divided between the two channels. In one embodiment, the A/D board includes an 8 Kb memory divided between the two channels.

The RF board processes and displays RF signals, including full wave rectified, positive half wave rectified and negative half wave rectified signals. The RF rectification portion of the ultrasonic board 164 accepts input from an external RF source or other sources having a voltage within the range of ±0.5 V. The data acquisition window for each channel is synchronized to the initial pulse or interface signal. The start point may be delayed up to 3 msec from the synchornization point.

The pulser receiver is a two channel device that generates and receives pulses from the ultrasonic transducer 134. The channels may be operated simultaneously or multiplex. The pulser receiver supports a pulse-echo, pitch-catch, or through transmission modes of operation for each channel. Each pulser, channel, contains a square wave and a spike pulser. The operator selects the pulser type to be used on a given channel.

The square wave pulser uses a digitally programmable negative going square wave pulser. In one embodiment, the square pulser provides pulse voltage over a range of 50 to 400 V with rise less than or equal to 14 nanoseconds and a fall time of 60 nsec. Rise and fall times are measured at 10% and 90% amplitude points into a 100 ohm resistive load. The operator selects the pulse width over a range of 80 nsecs to 1 $\mu$sec in 20 nsec steps is provided. The operator also selects pulser damping settings in four distinct steps over the range of 50 to 400 ohms, inclusive. The spike pulser uses a digitally programmable spike pulser. In one embodiment, the spike pulser provides pulse voltages over a range of 50 to 400 V.

The multiplexed ultrasonic receiver receives and processes input signals. In one embodiment, the receiver has a frequency response of 0.5 to 30 MHz at −6 dB and 40 dB gain. The receiver provides 0 to 98 dB of gain in increments of 0.5 dB (−40 dB to +58 dB). Maximum error per 10 dB increment is measured at less than or equal to ±1.5 dB with a total error over the entire range measured at less than or equal to ±2.0 dB.

The receiver contains high pass and low pass filters. The filters may be used separately or in combination to produce a specific band pass filter. The receiver includes sufficient sensitivity and noise level capabilities. In one embodiment, receiver sensitivity is measured with a 200 $\mu$V peak to peak input signal and produces a corresponding full scale screen signal with a signal-to-noise ratio of 3 dB, when operated, for example, at 10 MHz low pass filter mode. The noise level does not exceed 40% grass level on screen at maximum gain.

Each receiver channel includes a DAC. The DAC is active over the entire acquisition time with each channel being independently controllable. The DAC utilizes up to 16 operator selectable segments with each segment being adjustable in width and slope. The operator through the software graphical interface selects the appropriate points for establishing the DAC curve. Each point is independent and can provide a positive or negative gain within the range of −20 dB to +58 dB. Overall DAC range is 38 dB within the overall receiver gain range. The maximum slew rate per segment is 24 dB per $\mu$sec.

The ultrasonic board 164 also contains both hardware and software gates, as discussed above. The ultrasonic board 164 includes four software flaw gates, two hardware flaw gates, one interface gate and one back-tracking gate per channel. The operator sets the delay and duration of the gates. The display is provided in both real time and metal path time.

With respect to the hardware gates, the ultrasonic board 164 includes one interface gate per channel and two dedicated flaw gates per channel. The operator may independently adjust the gate start position and width over the entire data acquisition range. The flaw gates acquire and store peak and time-of-flight data only. Operator selections are provided for acquiring the first signal amplitude in the gate, maximum peak signal in the gate, first signal amplitude above a selected threshold, and time-of-flight of the signal for any selected analysis mode.

The flaw gates are adjustable in position and width over the entire acquisition range. The settings for each flaw gate are digitally displayed in the gate calibration window. The display is also viewable by positioning of the system display cursor at a desired location on the display monitor. The flaw gate may be set to function over an operator selectable data acquisition delay. Gate delays are synchronized using either the initial pulse or the interface gate.

The ultrasonic board 164 also provides hardware for video detection. In one embodiment, the video board is a VGA color board; however, other board types may be used. This hardware permits positive, negative, or full wave video signal or complete RF signals to be recorded and stored. Additionally, the hardware is associated with software that displays video signals while acquiring and storing RF waveforms.

The ultrasonic board 164 further includes hardware run length encoding for reducing data file size and increasing data acquisition rates. The data compression feature includes a threshold selection feature that provides noise suppression of displayed and acquired data, thus, also serving as a linear reject function. The data compression algorithm is discussed more fully below.

The ultrasonic board 164 includes software (discussed more fully below) and hardware that permit measurement of material thickness. In particular, the ultrasonic-board 164 components permit measurement of the thickness of aluminum down to 0.012 inches and reliably resolves a change in graphite/epoxy composite. In one embodiment, the ultrasonic board 164 resolves graphite/epoxy composite structures ranging in thickness from 1 ply to 120 plies.

The ultrasonic board 164 meets the horizontal and vertical linearity requirements stated herein when tested in accordance with paragraph 5.2 of ASTM E317-85 and method B defined in paragraph 5.3.3 of ASTM E317-85, both incorporated herein by reference.

The ultrasonic board 164 meets the near surface and depth resolution requirements described herein when tested in accordance with the following procedure. In both tests, the reject is in the "off" position, and aluminum ASTM blocks are used.

The ultrasonic board 164 satisfies the resolution requirements of Paragraph 5.4 of ASTM E317-85, incorporated herein by reference, when tested in accordance with the method outlined in this paragraph using the frequencies, transducer 134 diameters, ASTM hole sizes and hole depths stated in Table 1 below. The 80% and 20 specified in Paragraph 5.4 shall be changed to 1000% and 10%, respectively. The indication from the flat bottom hole is clearly distinguishable from the initial pulse. The peak amplitude of this signal meets the peak to valley ratio stated in Table 1 when compared to the initial pulse trailing edge valley amplitude. With the transducer 134 positioned away from the flat bottom hole, the resulting baseline signal amplitude, in the area of the hole signal, is such that the stated peak to valley ratio is also met when compared to the hole signal amplitude.

TABLE 1

RESOLUTION

| Frequency (MHz) | Transducer Diameter (inches) | ASTM Hole Size (aluminum block) | Hole Depth Below Surface (inches) | Peak-Valley Ratio | Display Mode |
|---|---|---|---|---|---|
| 2.25 | ½ | 5 | 0.100 | 10–1 | Full wave |
| 5.0 | ¼ | 5 | 0.050 | 10–1 | Full wave |
| 10.0 | ¼ | 2 | 0.050 | 10–1 | Full wave |
| 10.0 | ¼ | 1 | 0.050 | 7–1 | Any mode |

In addition to the sensitivity requirement set forth herein, the ultrasonic board 164 satisfies the sensitivity requirement of Paragraph 5.5 of ASTM E317-85, incorporated herein by reference, with the following modifications: (1) the reference level indications are 100% of full scale instead of 60%, (2) the required signal to noise ratio are as specified in Table 2 below, and (3) the reject is in the "off" position.

TABLE 2

SENSITIVITY

| Frequency (MHz) | Transducer Diameter (inches) | ASTM Block Number (aluminum) | Signal-Noise-Ratio | Gain Limit (% of maximum positive gain) |
|---|---|---|---|---|
| 2.25 | ½ | 2-0300 | 5–1 | 75 |
| 5.0 | 5/16 | 1-0300 | 5–1 | 75 |
| 10.0 | ¼ | 1-0300 | 10–1 | 80 |

The ultrasonic board 164 also satisfies the gain accuracy requirements specified herein when tested in accordance with Paragraph 6.22.2 of AWS D1.1-94 and Paragraph 5.6 of ASTM E317-85, both incorporated herein by reference.

Turning now to the eddy current board 166, the eddy current board 166 of the data acquisition and analysis system 22 uses a dual frequency dual channel card for acquisition of eddy current data. In one embodiment, the eddy current board 166 has a frequency range of 50 Hz to 4 MHz. The eddy current board 166 supports absolute, differential and driver pickup style eddy current probes.

The eddy current board 166 includes an A/D converter. In one embodiment, the A/D converter of the eddy current board 166 operates at a rate of 2,000 SPS for single channel operation and 1,000 SPS for multiple channel operation. The converter provides 12 bit resolution.

The eddy current board 166 also includes a driver and receiver. The driver permits adjustment of the drive voltage applied to the test coils. The exact voltage applied to the coils is a function of their nominal impedance and the excitation frequency. The operator selects the specific drive integer applied. The receiver adjusts the gain setting. In one embodiment, the gain is adjusted from 0 to 48 dB in controlled increments.

The eddy current board 166 is associated with software (discussed more fully below) and hardware that provide a display of a clear indication (a vertical deflection of the displayed screen, with an operator selectable signal to noise ratio of the vertical component). In one embodiment the vertical deflection ranges between 30–40% of the displayed screen. The accuracy of the display is measured using Air Force General Purpose Eddy Current Standard, Part No. 7947479-10 or AMS 4928, both incorporated herein by reference. These standards may be used to measure the performance for aluminum and titanium materials. It will be appreciated that other materials may be selected, and the test protocol modified accordingly.

In a faying surface, the eddy current board 166 provides a display of a clear indication (a vertical deflection of the displayed screen, with an operator selectable signal to noise ratio). The signal to noise ratio is determined by comparing average peak to peak signals over a defect free fastener hole to repeated scans over one with a defect present to obtain the average signal amplitude and the maximum width of the signal signature traces to obtain the noise amplitude. The inspection is conducted with the fasteners installed using a reflection or driver pickup type probe. Steel fasteners are highly susceptible to detection.

The eddy current board 166 uses dual frequencies to reduce unwanted signals from gaps between two 0.040 inch thick aluminum sheets. The eddy current board 166 produces a minimum of 20% of the displayed screen for a wall loss, of 10% originating on the rear side of the second layer. The wall loss signal to gap signal ratio is greater than or equal to four. The gap variance range is 0.000 to 0.025 inches. The ratio of the electrical noise, with the probe stationary, is 10 to 1 compared to the 10% wall loss signal. The eddy current board 166 indicates a faying surface 10% wall thickness loss over a one inch diameter area in an aluminum plate with thicknesses up to 0.120 inches.

The data acquisition and analysis system 22 also includes an external signal interface module. The external interface module accepts input signals from external NDI equipment for acquisition, display and storage. The input is through the ultrasonic board 164 via the A/D converter. The sample rate can be varied as required.

In one embodiment, the module converts external signals within a ±10 V amplitude range to a compatible range of ±0.5 V for input to the ultrasonic board 164 A/D converter. The converted signals are displayed from 0–100% of full screen height through the use of the system receiver gain, and provides a vertical linearity within 5% of full scale. The input impedance is also converted to obtain compatibility with the A/D converter. The input connector is of the standard BNC type.

Turning now to a discussion of the data acquisition and analysis system 22 software subsystem 150, the software subsystem 150 includes various software files that control the operation of the scanner 10. The software subsystem 150 stores processor setup, operating and image display parameters on a selected file for easy reference. In essence, the software subsystem 150 files store the operating parameters for controlling scanner 10 functions. In operation, the files permit various types of information to be retrieved and evaluated regarding the integrity of the surface under inspection. This information includes ultrasonic, eddy current, as well as other NDI generated data. Upon loading an existing file, the operator may repeat any previous scan or rapidly alter the system configuration to perform a new scan.

The software subsystem 150 files include data correction functions that correct for offsets in adjacent data strokes due to mechanical hysteresis. The operator inputs an integer value and the software shifts every other stroke by this value.

One version of the software subsystem 150 files is UNIX based, and is displayed on the display screen of the host computer 154 using an X-Windows™/Motif based format. It will be appreciated that other software formats may be used. The UNIX based format provides the operator the ability to adjust the size of any display window, adjust the number of open windows, and adjust the layering of the windows as desired. As discussed above, user interface is achieved using the keyboard 160 or a pointing device 157 such as a mouse. As previously discussed, the operator executes commands through the use of pull-down and/or tear-off menus.

The software subsystem 150 permits transferring data files via modem or LAN to another computer or device for post analysis or review. To further facilitate review of the stored data or processed information, the software subsystem 150 includes files for converting data to commonly used data formats, including but limited to, TIFF format files. If a TIFF converter is used, the files may be reviewed and analyzed on a separate computer. In one embodiment, National Institute of Health image analysis software, version 1.52 or equivalent may be used to analyze the data.

With respect to ultrasonic, time-of-flight, amplitude and raw inspection data, the data may be formatted into separate TIFF files. With respect to eddy current and other NDI instrument files, the raw data and image files may be formatted as separate TIFF files. The TIFF files may be converted to other formats, for example MS-DOS or PC compatible, without the loss of data or a reduction in the data's quality.

Additionally, the files include real-time multi-tasking with a graphical user interface. The multi-tasking capabilities permit an operator to analyze a file, print images from that file, and acquire data simultaneously. The files also provide for computer 154 realignment of possible skewed data from scanner mechanical hysteresis resulting from bi-directional scanning.

The following discussion describes the hardware subsystem 152 and the software subsystem 150 capabilities in the calibration mode. With regard to ultrasonic calibration, the data acquisition and analysis system 22 provides the operator with control over scanner 10 related functions, including movement, position, and scan parameters. The operator also has control over the scanner 10 settings. Functions controlled in the calibration mode include gate and channel selection, data acquisition type selection, signal processing selection, data compression, distance amplitude correction (DAC), pulser preamp adjustment, gate adjust, and A-scope.

With regard to gate and channel selection, the operator chooses which channel and gates to be utilized during data processing. As previously discussed, the ultrasonic board 164 includes two channels. Each channel has four software flaw gates, two hardware flaw gates, one interface gate, and one back-tracking gate.

Since the operator has control over the type of data selected for processing, the operator can configure the system to record full RF, video or peak and time of flight data. The operator may adjust the A/D rate to discrete values as, discussed above, between one and 100 MSPS, inclusive.

With regard to signal processing selection, the operator selects the signal processing method used. The operator may also choose to activate the data compression algorithm. The data compression algorithm is based on amplitude and duration. The RF data must be below the defined amplitude for the number of defined data points for compression to occur. This ensures that the complete decay of actual signals will be recorded. RF values of zero are substituted for the data points when the data compression occurs. The result is a significant reduction of the data file size.

Additionally, the operator has control over the distance amplitude correction (DAC) function. This function allows the operator to apply a correction that adjusts the gain applied to the data as a function of time and to normalize the amplitude response of signals over time. In one embodiment, the data acquisition and analysis system 22 provides 38 dB of dynamic range for the DAC gain. This gain is limited so that the total effective gain is within the 0 to 100 dB of system gain.

With regard to pulser preamp adjustment, the operator first selects either the square wave pulser or the spike pulser. Secondly, the operator selects the voltage applied by the pulser and the width of the square wave pulser. Next, the operator selects the damping, filtering and gain parameters to be applied.

The operator also configures the screen display 158 to provide a standard A-scan format of the type normally displayed on manual CRT ultrasonic instruments. The display 158 provides a plot of percentage full screen height versus time. The operator uses this display to perform initial system calibration. In this mode, the operator has control over the selection of the ultrasonic parameters, including delay and duration of gates, A/D rate, gain, pulse voltage and duration, and transducer 134 mode. The operator interactively adjusts these parameters until the proper calibration is achieved.

The operator also adjusts a variety of display features from the calibration menu, including rotation, amplitude scale, cursor width, vertical to horizontal ratio, and vertical strip chart time scale. These features may be adjusted prior to or after data is acquired. Additionally, the operator performs multifrequency mixing to suppress undesired signals by selecting the signal to suppress and performing the mix in the calibration mode.

The eddy current board 166 permits the setting of a hardware null and a selectable software null to define a data display/computer reference point. The operator sets the hardware null in the calibration mode by performing a hardware balance. The operator adjusts the eddy current board 166 settings so that the probe operating point is at the center of the total impedance dynamic range.

The operator also adjusts the center reference point during or after data acquisition. The cursor location is defined as the null point. The scanner 10 display features are based on this null point, and C-scans are computed based upon how the given data point differs from this null point.

The operator also has control over other eddy current calibration features. In the eddy current calibration mode, the data acquisition and analysis system 22 acts as a standard impedance plane eddy current instrument. The operator adjusts eddy current related functions from a calibration menu selectable from the pull-down menu. Through the calibration menu the operator adjusts the operating frequency, probe type, gain and coil voltage. In one embodiment, the operating frequency ranges between 50 Hz and 4 MHz, and the probe type is an absolute, differential or driver/pickup. The gain is set between 0 and 48 dB, inclusive, and the coil voltage ranges between 1 and 16 V, inclusive.

In the eddy current calibration mode, the operator also adjusts the scan control features. The standard method of inspection is to perform boustrophedonic (bi-directional or meander) scans. The operator defines a scan pattern by specifying the stroke length step and index range, along with the sampling grid spacing between pulses. The start and stop point for a scan may be any value. This allows the origin for the scan to correspond to some reference datum point on the component being inspected.

The data acquisition and analysis system 22 includes a variety of analysis features, each of which will be discussed below. The data display capabilities of the data acquisition and analysis system 22 permits rapid review of the data for possible reportable indications. Consequently, the operator can concentrate on performing a detailed review of these indications. The data is displayed in either metric or English units of measure.

The data acquisition and analysis system 22 permits adjusting the content and scale of the analysis screen display. The operator independently adjusts the area of the display used for each of the four major analyses screen elements: legend, C-scan, B-scan and A-scan. The legend displays system configuration parameters such as file name, scan parameters, ultrasonic parameters.

The C-scan display is a plan top view of data within a specified C-gate. The operator chooses what slice(s) to display by adjusting the C-gate or by selecting a different C-gate. The operator may perform this function at any time without repeating the scan. Additionally, the operator displays the parameter of interest using a variety of colors selectable from the palette. The operator may alter the color palette as well as add values associated with the color(s) selected.

The C-scan display presents the C-scan as either a peak, time-of-flight, decibel, threshold peak, depth, or polarity display. When displayed as a peak, the amplitude C-scan color codes and displays the maximum rectified amplitude in the C-gate for each waveform. In the time-of-flight mode, the C-scan color codes and displays the time-of-flight for a signal in the C-gate for each waveform. The time-of-flight is selected as either the time to the first threshold crossing or the maximum signals within the C-gate. If multiple and equal maxima are encountered, the first maximum is used. The data can be expressed in terms of time, depth, and metal path or in any other appropriate manner.

With regard to time-of-flight, this function measures the thickness of a surface under inspection as described above for the ultrasonic board 164. Two separate types of results are provided. The first provides the location and value of the maximum and minimum wall thickness. The second provides the percentage of area with a thickness reading greater than and less than a user specified minimum thickness threshold.

Additionally, when the C-scan is presented as a decibel scale, data is displayed as amplitude values relative to an operator defined FSH percentage. As a threshold peak, the C-scan is the same as the peak C-scan except any data point with a value below an operator specified threshold is plotted as background color. Using the depth type display, the C-scan is based on the time-of-flight data but uses inches instead of microseconds for the color map. The velocity of the sound value and the wedge delay are used to calculate the depth. The maximum and minimum depth values correspond to the start and stop of the C-gate. Finally, as a polarity display, the color map provides an amplitude map with the colors differentiating between positive and negative going signals. The polarity C-scan type is effective if RF data recording was selected.

The operator may define the upper and lower limit for the color scale used for any given C-scan type. Any value above or below the selected limits is assigned a specified color value. The color scale used with the C-scan will be a linear distribution between the defined upper and lower limits.

The operator may select from a variety of existing color pallets for use with the C- and B-scans. The operator may also modify an existing pallet to generate a new pallet.

Additionally, the data acquisition and analysis system 22 includes software associated with the ultrasonic board 164 for analyzing synthetic aperture focusing to correct B- and C-scan displays for beam profile parameters, and C-scan RF signal leading edge polarity (at zero crossing) display of either a maximum or minimum, above a selectable threshold, signal in a specified A-scan gate or first signal, above a selected threshold, in an A-scan gate. The data acquisition and analysis system 22 also includes software associated with the ultrasonic analyzer 164 for performing ratio analysis of selected peak amplitude signals or integrated rectified signals from two separate independent gates to determine relative disbond/good bond signal decay rates.

The data acquisition and analysis system 22 includes zoom capabilities. The data acquisition and analysis system 22 uses a maximum of "n" compression algorithms to display images. This routine is used when the number of data points is larger than what can be shown on the screen area assigned to the image. The operator can zoom the C-scan image to display the acquired data points.

The data acquisition and analysis system 22 includes a scroll feature that permits an operator to view a C-scan having a size that exceeds the screen display limits. For such a C-scan, only a portion of the C-scan is displayed at a time. The scroll feature allows the operator to pan across the entire data display. The data acquisition and analysis system 22 also permits the operator to swap the display axis of the C-scan data.

The data acquisition and analysis system 22 also includes software files for performing statistical analyses on an operator selected portion of the C-scan. The statistics calculations performed include time-of-flight and amplitude based analyses.

Amplitude statistics examine amplitude measurements. Again, two types of results are provided. The first provides the location and value of the maximum and minimum amplitude values above an operator specified threshold. The second provides the percentage of area with an amplitude reading greater than and less than an operator specified value.

Further, the data acquisition and analysis system 22 includes an interleave function. This function allows the operator to combine data obtained from separate transducers 134 into a single image. Specifically, this function merges the peak and time-of-flight data from channels 1 and 2 of the same data file.

Turning now to B-scans, a B-scan is a graphic presentation of a section view. The B-scan display uses the same color palette as the amplitude C-scan to represent the amplitude of the waveform for each discrete data point recorded through time.

The data acquisition and analysis system 22 includes a cursor for moving through the B-scan. The operator uses the cursor to select a waveform (A-Scan). The wave form is displayed below the B-scan. In addition, the operator uses the cursor to select a specific data point to find the peak within the active C-gate. The data acquisition and analysis system 22 graphically displays the incident skew angles in the B-scan.

The data acquisition and analysis system 22 permits the operator to display the B-scan using colors selected from the color palette or using various shades of gray, also selected from the color palette. The operator performs time-of-flight tip defraction analysis while using a polarized gray scale in the B-scan.

The data acquisition and analysis system 22 B-scan display includes a zoom function, and uses a maximum on "n" compression algorithms to display images. This routine is used when the number of data points is larger than what can be shown on the screen area assigned to the image. The operator zooms the B-scan image to show the acquired data points.

The data acquisition and analysis system 22 includes a scroll feature that permits the operator to view a B-scan having a size that exceeds the screen display limits. For such a B-scan, only a portion of the B-scan is displayed at a time. The scroll feature allows the operator to pan across the entire data display. Additionally, the operator may adjust the B-scan for curvature correction. This function adjusts the depth, metal path, and surface position to correct for the effect of a curved surface.

For B-scan data, the data acquisition and analysis system 22 includes timebase time-of-flight and metal path selection functions. These functions let the operator display the scan in terms of time or distance. The display screen shows the chosen units. With regard to the metal path, the zero depth-position is defined by the wedge delay.

The operator performs measurements on signals on the B-scan using a calibrated measurement function. The system uses two measurement cursors. The first is the reference line, and the second is the measurement line. The calibrated measurement function can be used in two ways. The first is to perform a delta measurement. For this application, the operator places a dotted cursor at one position and a solid cursor at a second position. The distance between the two is displayed. The second is to perform a calculated depth measurement. This is used to define depth measurements based on operator selected signals. The operator selects any point within the B-scan and defines the actual depth of this point. This function is generally used when normal measurement values are not accurate.

The data acquisition and analysis system 22 also includes a weld overlay function. This function displays a pictorial representation of the weld on the B-scan display, and helps identify reflectors generated due to weld geometry. Additionally, the data acquisition and analysis system 22 includes software for performing Fast Fourier Transform (FFT) analysis on selected waveforms in the B-scan (FFT may also be used for C-scan analysis).

The data acquisition and analysis system 22 also uses synthetic aperture focusing techniques (SAFT) to simulate the focal properties of a large-aperture, focused transducer 134 using data acquired with a small-aperture transducer 134 that has been scanned over a large area. Line SAFT, a two-dimensional version of SAFT, is performed on-line and in the field. Line SAFT generally requires significantly fewer calculations than three-dimensional SAFT.

The data acquisition and analysis system 22 includes software and hardware for displaying B'-scans. The display features discussed for the B-scan are included as elements of the B'-scan display.

With regard to A-scans, an A-scan is a graphic representation of the recorded RF waveform. The A-scan is displayed in either video or RF mode. The data acquisition and analysis system 22 via the ultrasonic board 164 supports RF, full wave rectified and positive and negative half wave rectified data. To display positive and negative half wave rectified data, the data must be acquired in the desired half wave mode.

The data acquisition and analysis system 22 includes a variety of eddy current analysis features, each of which shall now be discussed. The data display capabilities of the data acquisition and analysis system 22 are designed to allow rapid review of the data for possible reportable indications. The operator, thus, can concentrate on performing a detailed review of these indications, and performing an analysis of the data at any time on any file, including during data acquisition. The data acquisition and analysis system 22 displays the data in either metric or English units.

For example, the eddy current analyzer 166 includes software that permits simultaneous presentations of impedance plane, sweep and C-scans so that the operator can monitor the scan images and signal data as they are generated. The analysis includes C-scans based on impedance magnitude, impedance phase, horizontal impedance component, and vertical impedance component. The impedance phase C-scan is calibrated in degrees and the other C-scans are based on percent of full dynamic range. The analysis provides for C-scans based on the spatial derivative of above C-scans to characterize signals representing a high rate of change in phase and magnitude.

The analysis also provides for impedance plane displays and corresponding sweep displays of the vertical and horizontal impedance components. The data acquisition and analysis system 22 stores the digitized impedance data along with positional information. This method of data storage permits the generation of the type of C-scan displays discussed below along with the creation of synthesized strip charts and impedance plane displays. The screen is configured for combinations of simultaneous data displays, including up to two different C-scans and an impedance plane display. The data acquisition and analysis system 22 provides the ability to adjust the content and scale of the analysis screen display.

Since the raw data is stored, post inspection software parameters such as, but not limited to, phase, vertical/horizontal scaling may be varied and the corresponding C-scans, sweeps and impedance planes recomputed. An analysis is provided for variable vertical horizontal amplitude ratio scaling. Dual frequency mixing is displayed in the impedance plane format. The operator adjusts the area of the display used for legend and C-scan information. The legend displays system configuration parameters such as file name, scan parameters, and eddy current parameters.

As with ultrasonic data, the C-scan is a top plan view of the data. For each channel of acquired data, the operator displays a choice of C-scan types, discussed below, for each channel. The parameter of interest is displayed using color (s) selected from the color palette. The operator may alter the color palette used as well as the values, if any, associated with each color.

The type of C-scan displays that may be generated include horizontal amplitude, vertical amplitude, magnitude, phase, and first spatial derivative. For horizontal amplitude, the horizontal component of the impedance plane data is plotted relative to the operator defined center value. The data displayed is plotted in terms of eddy current units (ECU).

The eddy current board 166 used with the system has a total digital dynamic range of ±4K. One data point of that dynamic range equals one ECU. Thus, the ECU provides a measure of the amplitude of the signal. As to the vertical amplitude, the vertical component of the impedance plane data is plotted relative to the operator defined center value. The data is plotted in terms of ECUs. The magnitude display, is a vector sum of the horizontal and vertical displays. The magnitude of the impedance plane data is plotted relative to the operator defined center value, and the data is plotted in terms of ECUs.

The phase display is plotted as the phase angle of the impedance plane relative to an operator defined center. The data is plotted in terms of degrees. The operator specifies a magnitude threshold for use with the phase C-scan. The magnitude of any given data point must equal or exceed the threshold for the phase C-scan to display any color other than the "under" color. Finally, the first spatial derivative of any of the above four C-scans can be selected. The operator selects the number of data points over which the derivative is calculated.

In displaying the scans, the operator defines the upper and lower limits for the color scale used for any given C-scan type. Any value above or below the defined limits is assigned a specific color value. The color scale used with the C-scan will be a linear distribution between the defined upper and lower limits. The operator selects the desired color(s) using the color pallet. The operator may also modify an existing pallet to generate a new pallet.

The data acquisition and analysis system 22 includes a zoom function for displaying eddy current data. The data acquisition and analysis system 22 uses a maximum of "n" compression algorithms to display images. This routine is used when the number of data points is larger than what can be shown on the screen area assigned to the image. The operator zooms the C-scan image to show the acquired data points.

Another feature of the eddy current board 166 is a scroll function. The scroll function permits the viewing a C-scan having a size that exceeds the screen display limits. For such a C-scan, only a portion of the C-scan is displayed at a time. The scroll feature allows the operator to pan across the entire data display. The operator may also swap the display axis of the C-scan data using the swap axis function.

The eddy current analyzer 166 includes a lissajous display. Complex impedance data for a specified channel is displayed using the lissajous display. The cursor location and width define the data displayed. The operator, thus, can display the actual data value for any C-scan type and channel.

Additionally, the eddy current analyzer 166 includes a vertical/horizontal (V/H) ratio function for applying separate scaling factors to the horizontal and vertical components of the signal. This is accomplished using the V/H parameter. This variable is a post acquisition item. The V/H parameter effects strip charts, lissajous displays and C-scans, and is useful in increasing the phase separation between lift-off signals and small near surface flaws.

The eddy current analyzer 166 also includes high and low pass filters for treating the eddy current data. The filters are applied to the acquired data. Another feature of the eddy current analyzer 166 is a depth indication merge (DIM) file. The DIM file combines data obtained from separate channels (transducers) and/or files inspecting the same volume at different skew and/or inspection angles. The results provide C- and B-scans of the data where the colors indicate which channel or combination of channels have an indication above a specified threshold.

The data acquisition and analysis system 22 provides C-scan measurements of defect parameters, including, but not limited to, width, length, area, minimum/maximum defect spacing, defect to non-defect area percentage over a defined area, mean, standard deviation, X-Y location on the part being inspected. Additionally, the data acquisition and analysis system 22 generates B-scan measurement of parameters, including, but not limited to, defect depth, length/width, part thickness, and percent remaining part thickness.

The data acquisition and analysis system 22 includes a C-scan histogram function that lets the operator select an area of the C-scan with a "rubber-band box". The data in the selected area is compiled and displayed such that the number of occurrences of data in each data range is indicated in the form of a histogram chart.

Finally, the scanner 10 includes a portable scanner 168. The portable scanner 168 is compatible with the data acquisition and analysis system 22 of the scanner 10. Like the automated scanner 10, the portable scanner 168 is capable of ultrasonic and eddy current inspections. The X- and Y-axes of the portable scanner 168 may be locked to facilitate rectilinear scanning. Additionally, as with the automatic scanner 10, the portable scanner 168 is adapted for use on curved surfaces, and is capable of being vacuum loaded to the surface to be inspected.

It will be appreciated that the scanner 10 has been described in accordance with the illustration shown in FIGS. 1–10, and may include operational and functional characteristics other than those described.

Installation

To facilitate installation of the inspection system 10 by a single operator, each axis 28, 30 and 32 may be loaded independently. Further, each axis tractor 82, 84 and 86 may be loaded independently of its respective track assembly 28, 30, and 32. The following procedure may be used to install the scanner 10. For illustration purposes, the selected inspection area for the stated procedure is four feet along the X-axes 28, 30 and six feet in the Y-axis 32 direction. The operator installs the master X-axis 28 on the surface to be inspected. The master X-axis 28 tractor assembly 82 is installed on the X-axis vacuum track 28 assembly. The operation then installs the slave X-axis track assembly 30. This installation is followed by the installation of the slave X-axis tractor assembly 84 onto the slave X-axis track assembly 30. The operator next secures the Y-axis track assembly 32 to the master and slave X-axis tractor assembly 82, 84 using quick disconnect coupling. The Y-axis tractor 86 and thruster assembly 18 are installed on the Y-axis track assembly 32. Next, the operator connects the umbilical cable assembly 26 to the scanner 10. The scanner 10 is also tethered to an external surface to prevent damage in the event the scanner 10 becomes inadvertently detached from the inspection surface.

Operation

After scanner 10 installation is complete, the operator drives the NDI probe(s) 134 to the zero or starting position using the handheld joystick 157' and zeros the encoders by pressing a single control. If a scan plan has not been taught, the operator accomplishes teaching the inspection area as described herein. If a scan plan has already been taught, the operator inputs the scan plan via an applicable file name.

If performing an ultrasonic inspection, the system prompts the operator to enable the couplant supply system 24 prior to scanning and to disable the couplant system 24 at the termination of the scanning sequence.

Upon operator initiation of a scan cycle, the scan control subsystem 20 drives the scanner 10 back to the zero position (if not already at this position) and commences the scanning operation upon operator command. The operator selects the format for displaying the data. For instance, the operator selects real-time amplitude based or time-of-flight based C-scans or selects to display the RF waveform data. A C-scan is generated for each gate utilized per channel, though only one C-scan at a time is displayed.

The data acquired at each grid point is displayed (a C-scan and an A-scan) in near real-time. This provides direct visual feedback of both scanner location and direction. In addition, the quality of the data may be verified. Additionally, the scanner 10 is monitored for slippage by using a close loop tolerance technique. Excess slippage or drift causes the system to automatically terminate the scan and provide an error message.

As discussed above, the movement of the scanner 10 assembly is controlled by an external three-axis scan control subsystem 20. The scan control subsystem 20 manipulates the NDI probes 134 using the preprogrammed rectilinear scan pattern. This scan pattern is referenced to the operator defined global coordinate system. The manipulation of the NDI probe 134 along the global axes is accomplished by coordinating the movement of the master X-axis tractor 82, slave X-axis tractor 84 and the Y-axis tractor 86 along their respective track systems 28, 30, and 32.

In controlling the scanner 10, the operator may enter a pause command, temporarily suspending the scanner 10 operation, at any time during the scan cycle. Additionally, the scan cycle may be terminated under three conditions: normal completion, operator termination and system termination. A normal completion occurs when the scanner 10 has completed the entire specified scan pattern. The operator may terminate the scan at any time, and the data acquired analyzed. However, when a scan is terminated before completion, the appropriate software subsystem 150 file is updated to provide a message that the scan was only partially completed. Finally, the system will terminate the scan upon detection of fault conditions, including scanner 10 slip, drift, or excessive velocity.

With respect to ultrasonic data acquisition, the data acquisition and analysis system 22 utilizes the scan pattern, ultrasonic calibration and eddy current calibration defined by the appropriate software file(s). During the ultrasonic data acquisition process, the scan control subsystem 20 moves the NDI probes 134 in the prearranged pattern as defined by the operator. At the specified coordinate positions (grid), the scan control subsystem 20 generates sync pulses. This causes the pulser to pulse and the ultrasonic board 164 to receive data.

This pulse on position technique results in the generation of ultrasonic waveforms at specified grid points. The data acquisition and analysis system 22 reads the full ultrasonic waveform, the video data, or the peak and time of flight information for each grid point. Additionally, the operator acquires multiple waveforms at each grid location as well as acquiring eddy current data simultaneously, multiplexed, with ultrasonic scans. Converted signals from other NDI equipment are collected in the same pulse on position manor.

Eddy current data acquisition occurs similarly. This activity is done simultaneously with ultrasonic data acquisition or separately, as the eddy current board 166 is continuously operating. When a sync pulse is received, the horizontal and vertical components of the impedance data for each active frequency and probe are recorded. The acquired data is stored in memory as a background task during data acquisition. This prevents loss of data due to AC power interruption.

There are a variety of configurations that may be employed to fabricate the scanner 10. Thus, the disclosed embodiment is given to illustrate the invention. However, it is not intended to limit the scope and spirit of the invention. Therefore, the invention should be limited only by the appended claims.

We claim:

1. A surface scanner comprising:
   a first flexible track assembly supporting a first motorized tractor assembly;
   a second flexible track assembly supporting a second motorized tractor assembly;
   a third track assembly supported by the first track assembly and the second flexible track assembly;
   a third motorized tractor assembly supported by the third track assembly;
   a thruster assembly supported by the third motorized tractor assembly;
   at least one inspection probe supported by the thruster assembly;
   scan control means for moving said at least one inspection probe over a surface to be inspected; and
   data acquisition and analysis means for acquiring data from said inspection probe related to a scan of at least a portion of said surface, and analyzing said data for defects in said surface.

2. The surface scanner as defined in claim 1, wherein the first flexible track assembly and the second flexible track assembly include a plurality of interconnecting track plates.

3. The surface scanner as defined in claim 2, wherein the track plates are flexible members, said track plates do not plastically deform upon bending and twisting.

4. The surface scanner as defined in claim 3, wherein the interconnecting track plates are fabricated of spring steel.

5. The surface scanner as defined in claim 3, wherein the track plates are adjusted to mate with complex surface configurations.

6. The surface scanner as defined in claim 5, wherein the track plates are adjusted to mate with aircraft surfaces.

7. The surface scanner as defined in claim 1, wherein the first flexible track assembly and the second flexible track assembly support a plurality of vacuum cup assemblies coupled to a vacuum source.

8. The surface scanner as defined in claim 7, wherein the scanner includes a warning for alerting an operator of a loss of vacuum pressure.

9. The surface scanner as defined in claim 8, wherein each vacuum cup forming the plurality of vacuum cup assemblies includes a mounting hinge for adjusting the angular position of the vacuum cup assembly.

10. The surface scanner as defined in claim 1, wherein the first flexible track assembly and the second flexible track assembly support end of travel stops at each end thereof.

11. The surface scanner as defined in claim 1, wherein the first flexible track assembly and the second flexible track assembly each supports gear racks.

12. The surface scanner as defined in claim 11, wherein each gear rack receives a mating gear supported by the respective tractor assembly.

13. The surface scanner as defined in claim 12, wherein the mating gear is a pinion gear.

14. The surface scanner as defined in claim 13, wherein the pinion gear is motor driven.

15. The surface scanner as defined in claim 1, wherein the first tractor assembly and the second tractor assembly support a plurality of guide rollers for engaging, respectively, the first flexible track assembly and the second flexible track assembly.

16. The surface scanner as defined in claim 1, wherein the first tractor assembly and the second tractor assembly support at least one clamping handle for respectively coupling the first tractor assembly and the second tractor assembly to the first flexible track assembly and the second flexible track assembly.

17. The surface scanner as defined in claim 1, wherein the first tractor assembly and the second tractor assembly each supports an optical encoder.

18. The surface scanner as defined in claim 1, wherein the second tractor assembly includes a position adjustment mechanism for permitting movement along three axes of freedom relative to the third track assembly.

19. The surface scanner as defined in claim 1, wherein the third track assembly includes one track plate coupled to a rigid strut.

20. The surface scanner as defined in claim 19, wherein the third track assembly is fabricated with a spring steel track plate and aluminum strut.

21. The surface scanner as defined in claim 1, wherein the third track assembly supports end of travel stops at each end thereof.

22. The surface scanner as defined in claim 1, wherein the third track assembly supports a gear rack.

23. The surface scanner as defined in claim 22, wherein the gear rack receives a mating gear supported by the third tractor assembly.

24. The surface scanner as defined in claim 23, wherein the mating gear is a pinion gear.

25. The surface scanner as defined in claim 24, wherein the pinion gear is motor driven.

26. The surface scanner as defined in claim 1, wherein the third tractor assembly supports a plurality of guide rollers for engaging the third track assembly.

27. The surface scanner as defined in claim 1, wherein the third tractor assembly supports at least one clamping handle for coupling the third tractor assembly to the third track assembly.

28. The surface scanner as defined in claim 1, wherein the third tractor assembly supports an optical encoder.

29. The surface scanner as defined in claim 1, wherein the surface scanner is lightweight.

30. The surface scanner as defined in claim 1, wherein articulating joints couple the third track assembly to the first track assembly and the second track assembly.

31. The surface scanner as defined in claim 30, wherein the joints permit non-parallelism and twist of the first track assembly and second track assembly relative to one another.

32. The surface scanner as defined in claim 30, wherein the joints are quick connect and disconnect couplers.

33. The surface scanner as defined in claim 1, wherein the third track assembly supports a master mounting bracket for permitting movement along multiple axes of freedom.

34. The surface scanner as defined in claim 33, wherein the master mounting bracket includes an angle dial plate.

35. The surface scanner as defined in claim 34, wherein the master mounting bracket includes an indicator for marking the angular position of the angle dial plate.

36. The surface scanner as defined in claim 35, wherein the master mounting bracket includes a pivot mechanism for permitting a relative change in position of the third track assembly and the first track assembly.

37. The surface scanner as defined in claim 36, wherein the pivot mechanism includes an upper pivot block and a lower pivot block.

38. The surface scanner as defined in claim 1, wherein the scanner includes vacuum coupled fixturing for offsetting the first track assembly and the second track assembly from the edges of the surface to be inspected.

39. The surface scanner as defined in claim 1, wherein the third track assembly has a liner stroke of 6 feet.

40. The surface scanner as defined in claim 1, wherein the third tractor assembly supports a BNC connector array.

41. The surface scanner as defined in claim 1, wherein the third tractor assembly supports said thruster assembly for moving the scanner over the surface to be inspected.

42. The surface scanner as defined in claim 41, wherein the thruster assembly is supported by either the top or bottom surface of the third track assembly.

43. The surface scanner as defined in claim 42, wherein the thruster assembly includes a slide block for facilitating movement of the thruster assembly.

44. The surface scanner as defined in claim 1, wherein the third tractor assembly supports nondestructive inspection probes.

45. The surface scanner as defined in claim 44, wherein the third tractor assembly includes a gimbal for supporting one or more nondestructive inspection (NDI) probes.

46. The surface scanner as defined in claim 45, wherein the NDI probes include mechanical impedance, ultrasonic or eddy current NDI probes.

47. The surface scanner as defined in claim 45, wherein the inspection probes include a single transducer probe.

48. The surface scanner as defined in claim 45, wherein the inspection probes include an eddy current probe sled assembly.

49. The surface scanner as defined in claim 45, wherein the gimbal positively loads the inspection probes, keeping them in contact with the surface to be inspected.

50. The surface scanner as defined in claim 49, wherein the gimbal supports a gas spring for positively loading the inspection probes.

51. The surface scanner as defined in claim 50, wherein an interface block couples the gas spring to the gimbal.

52. The surface scanner as defined in claim 1, wherein the scanner further includes a plurality of inspection probes that are NDI probes and said scanner includes a couplant delivery system for supplying couplant fluid to the NDI probes.

53. The surface scanner as defined in claim 52, wherein the probes are ultrasonic probes and said couplant delivery system supplies couplant fluid to the ultrasonic NDI probes.

54. The surface scanner as defined in claim 52, wherein the couplant delivery system includes a delivery pump for circulating the couplant fluid, a supply tank for retaining the couplant fluid, and tubing interconnecting the pump, the supply tank and the NDI probes.

55. The surface scanner as defined in claim 54, wherein the couplant deliver system includes a filter for removing particulates from the couplant fluid.

56. The surface scanner as defined in claim 54, wherein the couplant delivery system further includes couplant retrieval gutters.

57. The surface scanner as defined in claim 52, wherein the data acquisition and analysis means includes a system for analyzing and storing the data acquired by the NDI probes.

58. The surface scanner as defined in claim 57, wherein the data acquisition and analysis system includes both hardware and software subsystems.

59. The surface scanner as defined in claim 58, wherein the data acquisition and analysis hardware subsystem includes a host computer.

60. The surface scanner as defined in claim 59, wherein the computer is portable.

61. The surface scanner as defined in claim 59, wherein the computer includes an Intel 486 DX2/66 MHz microprocessor.

62. The surface scanner as defined in claim 59, wherein the computer includes 64 Mb of RAM.

63. The surface scanner as defined in claim 59, wherein the data acquisition and analysis system includes an uninterruptible power supply.

64. The surface scanner as defined in claim 59, wherein the computer includes an outer chassis.

65. The surface scanner as defined in claim 64, wherein the chassis houses a keyboard.

66. The surface scanner as defined in claim 65, wherein the chassis supports a visual display for displaying the acquired and processed data from said data acquisition and analysis means.

67. The surface scanner as defined in claim 66, wherein the visual display is a VGA monitor.

68. The surface scanner as defined in claim 67, wherein the VGA monitor is a color monitor.

69. The surface scanner as defined in claim 64, wherein the chassis supports a pointing device.

70. The surface scanner as defined in claim 64, wherein the chassis includes ports for connecting to external devices.

71. The surface scanner as defined in claim 64, wherein the chassis includes ports for connecting to external devices.

72. The surface scanner as defined in claim 64, wherein the chassis supports a connection for a joystick.

73. The surface scanner as defined in claim 64, wherein the chassis supports a data storage means for storing said data.

74. The surface scanner as defined in claim 73, wherein the data storage means is a floppy disk drive.

75. The surface scanner as defined in claim 73, wherein the data storage means is an internal storage device.

76. The surface scanner as defined in claim 73, wherein the data storage means is a combination of an external storage device and an internal storage device.

77. The surface scanner as defined in claim 6, wherein the internal and external storage devices includes a 1.44 Mb 3.5 floppy disk drive in combination with a 500 Mb internal hard drive, and an external 1 Gb read/write optical drive.

78. The surface scanner as defined in claim 57, wherein the data acquisition and analysis means further cooperates with the scan control means, including a scan control system, for controlling the movement of the scanner.

79. The surface scanner as defined in claim 78, wherein the scan control system includes a scan control board.

80. The surface scanner as defined in claim 79, wherein the scan control board is a multi-axis controller, controlling movement of the first tractor assembly, the second tractor assembly, the third tractor assembly and the thruster assembly.

81. The surface scanner as defined in claim 80, wherein the scan control system includes software for controlling the function of the scan control board.

82. The surface scanner as defined in claim 81, wherein a scan pattern of the scanner is preprogrammed.

83. The surface scanner as defined in claim 82, wherein the scan pattern is programmed using a teach-and-learn technique for inputting data points that define the overall scan area and shape.

84. The surface scanner as defined in claim 82, wherein the scan pattern is programmed using a global coordinate system which permits referencing data points using identical coordinate systems laid-out on the actual surface to be inspected and the display of the scanned image.

85. The surface scanner as defined in claim 57, wherein the data acquisition and analysis means further includes an ultrasonic board for processing ultrasonic data.

86. The surface scanner as defined in claim 57, wherein the data acquisition and analysis means further includes a hardware subsystem having an eddy current board for processing eddy current data.

87. The surface scanner as defined in claim 57, wherein the data acquisition and analysis means further includes a software subsystem having software files for controlling scanner system operations.

88. The surface scanner as defined in claim 87, wherein the software subsystem includes software for performing ultrasonic data processing and analysis.

89. The surface scanner as defined in claim 87, wherein the software subsystem includes software for performing eddy current data processing and analysis.

90. The surface scanner as defined in claim 87, wherein the software subsystem includes software for performing mechanical impedance data processing and analysis.

91. A surface scanner comprising:
a first flexible track assembly supporting a first tractor assembly;
a second flexible track assembly supporting a second tractor assembly;
a third track assembly, one end thereof being supported by the first flexible track assembly and the opposite end being supported by the second flexible track assembly;
a third tractor assembly supported by the third track assembly;
a thruster assembly supported by the third tractor assembly;
one or more NDI probes supported by the thruster assembly for acquiring data concerning a surface to be inspected;
a scan control system for moving the NDI probes over the surface to be inspected; and
a data acquisition and analysis system for processing and analyzing the data acquired by the NDI probe.

92. The surface scanner as defined in claim 91, wherein the scanner includes a couplant delivery system for delivering couplant fluid to the NDI probes.

93. The surface scanner as defined in claim 91, wherein the NDI probes include ultrasonic, eddy current and mechanical impedance data probes.

94. The surface scanner as defined in claim 91, wherein the data acquisition and analysis system includes hardware and software subsystems for controlling scanner functions.

95. The surface scanner as defined in claim 91, wherein in the scan control system includes a global coordinate system for referencing data points on the surface under inspection and displaying an image correlated with said data points.

96. A method for installing a surface scanner comprising:
coupling a first track assembly onto a surface to be inspected;
drawing a vacuum pressure through vacuum cups supported by the first track assembly, creating a suction force adhering the vacuum cups to the surface;
coupling a first tractor assembly to the first track assembly;
coupling a second track assembly onto a surface to be inspected such that first track assembly is offset from the second track assembly;
drawing a vacuum pressure through vacuum cups supported by the second track assembly, creating a suction force adhering the vacuum cups to the surface;
coupling a second tractor assembly to the second track assembly;
coupling a third track assembly to the first track assembly and the second track assembly such that the third track assembly spans the gap between the first track assembly and the second track assembly;
coupling a third tractor assembly to the third track assembly;
coupling a thruster to the third tractor assembly, wherein the thruster supports NDI probes; and
controlling movement of said NDI probes over at least a portion of a surface to be scanned to acquire data from said NDI probes related to said scan.

97. The method of installing a surface scanner as defined in claim 96, wherein the step of controlling movement further includes step of an external data acquisition and analysis for controlling scanner functions.

98. The method of installing a surface scanner as defined in claim 97, wherein the step of data acquisition and analysis includes software for defining a global coordinate system for referencing a point on the surface inspected to an identical point on a corresponding scanned image.

* * * * *